Figure 1:
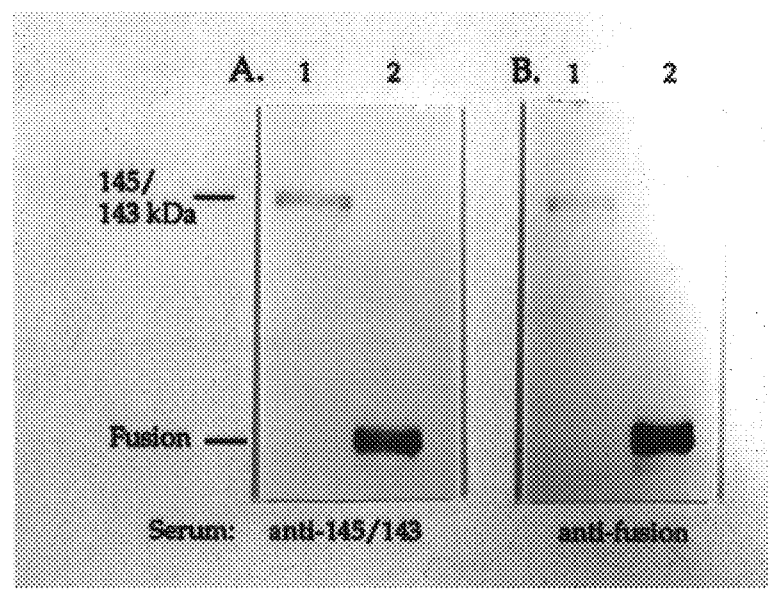

United States Patent [19]
Lamppa

[11] Patent Number: 6,117,666
[45] Date of Patent: Sep. 12, 2000

[54] PLASTID PROTEOLYTIC PROCESSING ENZYME THAT CLEAVES PRECURSOR POLYPEPTIDES

[75] Inventor: Gayle K. Lamppa, Chicago, Ill.

[73] Assignee: ARCH Development Corporation, Chicago, Ill.

[21] Appl. No.: 09/187,049

[22] Filed: Nov. 5, 1998

Related U.S. Application Data

[62] Division of application No. 08/695,177, Aug. 1, 1996.
[60] Provisional application No. 60/001,746, Aug. 1, 1995.

[51] Int. Cl.[7] .............................. C12N 9/50; C07H 21/04
[52] U.S. Cl. .................... 435/219; 435/212; 435/252.33; 435/320.1; 536/23.1; 536/23.2; 536/23.6
[58] Field of Search ..................................... 435/212, 219, 435/252.33, 320.1; 536/23.1, 23.2, 23.6

[56] References Cited

PUBLICATIONS

Abad, M. S., Clark, S. E. & Lamppa, G.K. (1989) Plant Physiol. 90, 117–124.
Abad, M.S., Oblong, J. E. & Lamppa, G. K. (1991) Plant Physiol. 96, 1220–1227.
Affholter, J. A., Fried, V. A. & Roth, R. A. (1988) Science 242, 1415–1418.
Authier et al. (Apr. 1995), Proc. Natl. Acad. Sci. USA, vol. 92, pp. 3859–3863.
Becker, A. B. & Roth, R. A. (1992) Proc. Natl. Acad. Sci. USA 89, 3835–3839.
Chen, N.–Y., Jiang, S.–Q., Klein, D. A. & Paulus, H. (1993) J. Biol. Chem. 268, 9448–9465.
Clark, S. E. & Lamppa, G. K. (1991) J. Cell. Biol. 114, 681–688.
Engler–Blum, G., Meier, M., Frank, J. & Müller, G. A. (1993 Anal. Biochem. 210, 235–244.
Finch, P. W., Wilson, R. E., Brown, K., Hickson, I. D. & Emmerson, P. T. (1986) Nuc. Acids Res. 14, 7695–7703.
Gavel, Y. & von Heijne, G. (1990) FEBS Letters 261, 455–458.
Gehm B. D., Kuo, W.–L., Perlman, R. K. & Rosner, M. R. (1993) J. Biol. Chem. 268, 7943–7948.
Guan, K. L. & Dixon, J. E. (1991) Anal. Biochem. 192, 262–267.
Hawlitschek, G., Schneider, H., Schmidt, B., Tropschug, M., Hartl, F.–U. & Neupert, W. (1988) Cell 53, 795–806.
Hirsch, S., Muckel, E., Heemeyer, F., von Heijne, G. & Soll, J. (1994) Science 266, 1989–1992.
Kuo, W. L., Gehm, B. & Rosner, M. R. (1990) Mol. Endo. 4, 1580–1591.
Lamppa, G. K. & Abad, M.S. (1987) J. Cell Biol. 105, 2641–2648.
Oblong, J. E. & Lamppa, G. K. (1992) EMBO J. 11, 4401–4409.
Paces, V., Rosenberg, L. E., Fenton, W. A. & Kalousek, F. (1993) Proc. Natl. Acad. Sci. USA 90, 5355–5358.
Perlman, R. K., Gehm, B. D., Kuo, W.–L. & Rosner, M. R. (1993) J. Biol. Chem. 268, 21538–21544.
Pierotti, A. R., Prat, A., Chesneau, V., Gaudoux, F., Leseney, A.–M., Foulon, T. & Cohen, P. (1994) Proc. Natl. Acad. Sci. USA 91, 6078–6082.
Rawlings, N.D. & Barrett, A. J. (1993) Biochem. J. 290, 205–218.
Robinson, C. & Ellis, R.J. (1984) Eur. J. Biochem. 142, 337–342.
Schnell, D. J., Kessler, F. & Blobel, G. (1994) Science 266, 1007–1012.
VanderVere, P., Bennett, T., Oblong, J. and Lamppa, G. (1995) Proc. Natl. Acad. Sci. USA 92, 7177–7181.
Witte, C., Jensen, R. E., Yaffe, M. P. & Schatz, G. (1988) EMBO J. 7, 1439–1447.
Yang, M. Geli, V., Oppliger, W., Suda, K., James, P. & Schatz, G. (1991) J. Biol. Chem. 266, 6416–6423.

*Primary Examiner*—Nashaat T. Nashed
*Attorney, Agent, or Firm*—Barnes & Thornburg

[57] ABSTRACT

A new soluble plastid processing enzyme is purified and characterized. cDNAs encoding the enzyme are isolated, allowing recombinant production of the enzyme. The enzyme cleaves precursor polypeptides that are targeted to organelles such as the chloroplasts. The enzyme is useful to produce mature, active proteins in vivo or in vitro. An example of the enzyme is a chloroplast processing enzyme (CPE) with specificity for cleavage that produces functional proteins.

6 Claims, 16 Drawing Sheets

Fig. 2(A)

SEQ ID NO. 1

```
                                                                       M  P
                                         SEQ ID NO. 13

GGATCCATTTCTGAGAAGTAGAAAGAAAAAAAAAATCTGAAAGAAAAATCAAGAGGTTGA          60
GTGCGTTGGTGTGCTTGCGTTTCTGTTAAGGTTAAGCTGCTACGCATACGGTGGTTATGC         120
                                                                       2
CAATGGCTGCTTCAACTTCAACCTCATCTCTCTCCGTCGTTGGAACTAACCTCTCTCTCC         180
  M  A  A  S  T  S  T  S  S  L  S  V  V  G  T  N  L  S  L  P          22

CTCCGCATCGTCATCATCGCCACTTTCACTCTCCCTCTTCAATCTCCACTCGTATCCGTA         240
  P  H  R  H  H  R  H  F  H  S  P  S  S  I  S  T  R  I  R  T          42

CCAACCGTCTCTTCTTATCCTCTTCTCTCGCGTTCTCTTCTCCACGTGATGCAAGAGTTG         300
  N  R  L  F  L  S  S  L  A  F  S  S  P  R  D  A  R  V  V            62

TTCACGCTGGATTAGGTTTACGGAGGAATACGCCGGATGTTTGGAAACACTATTCCTCCG         360
  H  A  G  L  G  L  R  R  N  T  P  D  V  W  K  H  Y  S  S  V          82

TCCTTTCTCAACCGACTGCACCGGTACCGGTACGGCAAAGCTGTACTTCATGCTGTCTTG         420
  L  S  Q  P  T  A  P  V  P  V  R  Q  S  C  T  S  C  C  L  A         102

CTTCCGCAAAGAAACGCCGTTCAAATCTCCCGAGATTTGTTCCTGGAGCTTTTTTTGATA         480
  S  A  K  K  R  R  S  N  L  P  R  F  V  P  G  A  F  F  D  S         122

GTTCTTCTTTTGGATTATCTAAGGATAAGCTTCGTCACGCTTCTGTTAAGCGGGTTCAGC         540
  S  S  F  G  L  S  K  D  K  L  R  H  A  S  V  K  R  V  Q  L         142

TTCCGCATGCAACTGTTGGTCCAGATGAGCCACATGCCGCTAGCACAACTTGGCAGGAGG         600
  P  H  A  T  V  G  P  D  E  P  H  A  A  S  T  T  W  Q  E  G         162

GCGTTGCTGAAAAACAAGACTTAAGTTTGTTTGATTCTGAACTGGAAAGGCTAGAGGGTT         660
  V  A  E  K  Q  D  L  S  L  F  D  S  E  L  E  R  L  E  G  F         182

TTTTGGGTTCTGAACTTCCATCTCACCCTAAGTTGCATCGGGGTCAGCTAAAGAATGGGA         720
  L  G  S  E  L  P  S  H  P  K  L  H  R  G  Q  L  K  N  G  I         202

TTCGTTATTTGATTCTGCCAAATAAAGTTCCTCCAACAAGGTTTGAAGCACACATGGAAG         780
  R  Y  L  I  L  P  N  K  V  P  P  T  R  F  E  A  H  M  E  V         222

TTCATGTAGGATCAATAGATGAAGAGGATGATGAACAAGGAATTGCACATATGATTGAAC         840
  H  V  G  S  I  D  E  E  D  D  E  Q  G  I  A  H  M  I  E  H         242
                                       SEQ ID NO. 12
ATGTTGCTTTCTTAGGAAGTAAAAAAACGCGAGAAGCTTTTGGGAACAGGAGCCCGTTCAA         900
  V  A  F  L  G  S  K  K  R  E  K  L  L  G  T  G  A  R  S  N         262

ATGCTTATACAGATTTTCACCATACAGTGTTTCACATCCATTCTCCTACCTCTACCAAGG         960
  A  Y  T  D  F  H  H  T  V  F  H  I  H  S  P  T  S  T  K  D         282

ATTCTGATGATCTTCTTCCATCTGTTCTGGATGCCCTGAATGAGATAACCTTCCACCCAA        1020
  S  D  D  L  L  P  S  V  L  D  A  L  N  E  I  T  F  H  P  N         302

ATTTTCTTGCATCAAGAATAGAAAAAGAACGGCGTGCTATACTCTCAGAGCTTCAAATGA        1080
  F  L  A  S  R  I  E  K  E  R  R  A  I  L  S  E  L  Q  M  M         322

TGAACACAATAGAGTATCGGGTTGATTGCCAGTTGTTACAACATTTGCATTCTGAAAACA        1140
  N  T  I  E  Y  R  V  D  C  Q  L  L  Q  H  L  H  S  E  N  K         342

AGCTGAGCAAAAGGTTTCCAATTGGATTAGAAGAACAGATAAAGAAGTGGGATGCAGATA        1200
  L  S  K  R  F  P  I  G  L  E  E  Q  I  K  K  W  D  A  D  K         362
```

```
AAATAAGAAAATTTCATGAGCGCTGGTATTTCCCTGCAAATGCAACATTGTACATTGTAG    1260
 I  R  K  F  H  E  R  W  Y  F  P  A  N  A  T  L  Y  I  V  G     382

GGGATATTGGTAACATTCCAAAAACTGTTAACCAGATTGAAGCTGTTTTTGGACAAACTG    1320
 D  I  G  N  I  P  K  T  V  N  Q  I  E  A  V  F  G  Q  T  G     402

GTGTAGACAATGAGAAAGGTTCTGTAGCCACTTCAAGTGCATTTGGTGCAATGGCTAGTT    1380
 V  D  N  E  K  G  S  V  A  T  S  S  A  F  G  A  M  A  S  F     422

TTCTAGTTCCTAAGCTCTCTGTTGGTCTTGGTGGAAATTCTATTGAAAGACCAACCAATA    1440
 L  V  P  K  L  S  V  G  L  G  G  N  S  I  E  R  P  T  N  T     442

CAACGGATCAATCAAAAGTATTTAAAAAGGAGAGACATGCTGTTCGTCCTCCTGTGAAGC    1500
 T  D  Q  S  K  V  F  K  K  E  R  H  A  V  R  P  P  V  K  H     462

ATACTTGGTCACTTCCTGGAAGCAGTGCAAATTTGAAGCCACCACAAATATTTCAACACG    1560
 T  W  S  L  P  G  S  S  A  N  L  K  P  P  Q  I  F  Q  H  E     482

AGTTGCTTCAAAACTTTTCAATTAATATGTTCTGCAAGATTCCAGTGAATAAGGTTCAAA    1620
 L  L  Q  N  F  S  I  N  M  F  C  K  I  P  V  N  K  V  Q  T     502

CATACCGAGATTTGCGTATTGTCTTGATGAAAAGAATATTTTTGTCAGCTCTTCATTTTC    1680
 Y  R  D  L  R  I  V  L  M  K  R  I  F  L  S  A  L  H  F  R     522

GTATTAATACGAGATATAAGAGTTCGAATCCACCATTCACTTCAGTTGAATTGGATCATA    1740
 I  N  T  R  Y  K  S  S  N  P  P  F  T  S  V  E  L  D  H  S     542

GTGATTCTGGAAGGGAAGGATGTACTGTGACCACTCTTACCATAACTGCAGAACCAAAGA    1800
 D  S  G  R  E  G  C  T  V  T  T  L  T  I  T  A  E  P  K  N     562

ATTGGCAGAATGCTATTAGAGTTGCTGTTCATGAGGTTCGCAGACTTAAAGAGTTTGGTG    1860
 W  Q  N  A  I  R  V  A  V  H  E  V  R  R  L  K  E  F  G  V     582

TTACTCAGGGTGAATTAACTCGCTATCTAGACGCCCTTTTGAGAGATAGCGAACACCTAG    1920
 T  Q  G  E  L  T  R  Y  L  D  A  L  L  R  D  S  E  H  L  A     602

CAGCCATGATTGATAATGTATCTTCTGTTGACAACTTGGATTTTATCATGGAAAGTGATG    1980
 A  M  I  D  N  V  S  S  V  D  N  L  D  F  I  M  E  S  D  A     622

CTCTAGGCCATAAAGTTATGGACCAGAGTCAAGGGCATGAAAGTTTAATTGCTGTTGCTG    2040
 L  G  H  K  V  M  D  Q  S  Q  G  H  E  S  L  I  A  V  A  G     642

GGACAGTTACCCTTGACGAGGTTAATTCTGTTGGTGCTCAGGTGTTAGAATTTATAGCTG    2100
 T  V  T  L  D  E  V  N  S  V  G  A  Q  V  L  E  F  I  A  D     662

ATTTTGGAAAGCTTTCTGCACCCCTTCCTGCAGCAATTGTTGCTTGTGTTCCGAAAAAAG    2160
 F  G  K  L  S  A  P  L  P  A  A  I  V  A  C  V  P  K  K  V     682

TTCACATCGAAGGAGCTGGTGAAACAGAATTCAAGATATCATCAACTGAAATAACAGATG    2220
 H  I  E  G  A  G  E  T  E  F  K  I  S  S  T  E  I  T  D  A     702

CTATGAAAGCTGGATTGGATGAGCCTATAGAGCCAGAACCCGAGCTCGAGGTTCCAAAAG    2280
 M  K  A  G  L  D  E  P  I  E  P  E  P  E  L  E  V  P  K  E     722

AACTTGTACAGTCATCAACGCTACAAGAGTTAAAAAATCAGCGCAAGCCAGCCTTTATTC    2340
 L  V  Q  S  S  T  L  Q  E  L  K  N  Q  R  K  P  A  F  I  P     742
```

```
CAGTCAGTCCTGAAATAGAGGCTAAGAAGCTTCATGATGAGGAAACTGGAATCACCCGCC    2400
  V  S  P  E  I  E  A  K  K  L  H  D  E  E  T  G  I  T  R  L     762

TCCGCCTTGCAAATGGAATTCCCGTCAACTATAAGATATCTAAAAGTGAAACACAAAGCG    2460
  R  L  A  N  G  I  P  V  N  Y  K  I  S  K  S  E  T  Q  S  G     782

GCGTGATGCGGCTGATTGTTGGTGGCGGACGAGCAGCTGAGGGTTCTGATTCAAGAGGAT    2520
  V  M  R  L  I  V  G  G  G  R  A  A  E  G  S  D  S  R  G  S     802

CTGTGATTGTGGGTGTTAGGACGCTTAGTGAGGGAGGTCGTGTTGGCAACTTCTCAAGGG    2580
  V  I  V  G  V  R  T  L  S  E  G  G  R  V  G  N  F  S  R  E     822

AGCAGGTTGAACTTTTCTGCGTAAATAACCAGATAAATTGCTCCTTAGAATCTACGGAGG    2640
  Q  V  E  L  F  C  V  N  N  Q  I  N  C  S  L  E  S  T  E  E     842

AGTTCATATCTTTGGAGTTTCGTTTTACTTTAAGGAATAATGGGATGCGTGCAGCCTTTC    2700
  F  I  S  L  E  F  R  F  T  L  R  N  N  G  M  R  A  A  F  Q     862

AATTGCTTCACATGGTGCTTGAGCATAGTGTCTGGTCAGATGATGCTTTGGATAGAGCGA    2760
  L  L  H  M  V  L  E  H  S  V  W  S  D  D  A  L  D  R  A  R     882

GGCAAGTGTATCTGTCATATTACCGATCAATCCCCAAGAGCTTGGAACGCTCGACTGCTC    2820
  Q  V  Y  L  S  Y  Y  R  S  I  P  K  S  L  E  R  S  T  A  H     902

ACAAACTTATGGTTGCAATGTTGGATGGAGATGAGCGATTTACTGAGCCTACACCAAGTT    2880
  K  L  M  V  A  M  L  D  G  D  E  R  F  T  E  P  T  P  S  S     922

CACTAGAAAATCTAACTCTGCAATCTGTTAAGGATGCTGTAATGAATCAGTTTGTTGGAA    2940
  L  E  N  L  T  L  Q  S  V  K  D  A  V  M  N  Q  F  V  G  N     942

ATAACATGGAGGTCTCCATTGTAGGTGATTTCACTGAGGAAGAGATTGAATCATGTATTT    3000
  N  M  E  V  S  I  V  G  D  F  T  E  E  E  I  E  S  C  I  L     962

TAGATTACCTTGGCACAGCTCAGGCCACGGGAAACTTTAAAAACCAGCAACAAATTATCC    3060
  D  Y  L  G  T  A  Q  A  T  G  N  F  K  N  Q  Q  Q  I  I  P     982

CACCAACATTTCGATTATCTCCATCCAGTTTGCAGTCTCAAGAAGTTTTCTTGAATGACA    3120
  P  T  F  R  L  S  P  S  S  L  Q  S  Q  E  V  F  L  N  D  T    1002

CTGATGAGAGGGCATGCGCTTATATTGCTGGGCCTGCACCAAACCGTTGGGGTTTTACTG    3180
  D  E  R  A  C  A  Y  I  A  G  P  A  P  N  R  W  G  F  T  A    1022

CAGATGGAAACGACCTGTTAGAGACAATTGATAATGCATCATCAGTCAATAATAATGGGA    3240
  D  G  N  D  L  L  E  T  I  D  N  A  S  S  V  N  N  N  G  T    1042

CAAAATCTGATGCTCTACAAACAGAAGGTGCTCCACGAAGGAGCCTCCGTAGTCATCCTC    3300
  K  S  D  A  L  Q  T  E  G  A  P  R  R  S  L  R  S  H  P  L    1062

TTTTCTTTGGTATAACAATGGGACTGCTTTCTGAAATTATAAATTCTAGGCTCTTCACAA    3360
  F  F  G  I  T  M  G  L  L  S  E  I  I  N  S  R  L  F  T  T    1082

CAGTCAGAGATTCACTGGGCTTGACATACGACGTGTCATTTGAATTGAACTTGTTTGATA    3420
  V  R  D  S  L  G  L  T  Y  D  V  S  F  E  L  N  L  F  D  R    1102

GGCTTAAACTAGGGTGGTATGTGGTCTCTGTAACATCAACTCCAAGCAAGGTGCACAAAG    3480
  L  K  L  G  W  Y  V  V  S  V  T  S  T  P  S  K  V  H  K  A    1122
```

```
CTGTTGATGCATGCAAGAATGTTCTAAGAGGTTTGCATAGCAACGGAATTACAGTCAGGG   3540
  V  D  A  C  K  M  V  L  R  G  L  H  S  N  G  I  T  V  R  E   1142

AATTGGACAGGGCTAAACGGACCCTTCTTATGAGACATGAAGCTGAAATTAAGTCAAATG   3600
  L  D  R  A  K  R  T  L  L  M  R  H  E  A  E  I  K  S  N  A   1162

CGTACTGGTTGGGATTGTTAGCTCACTTACAATCGTCTTCTGTTCCAAGGAAGGACCTAT   3660
  Y  W  L  G  L  L  A  H  L  Q  S  S  S  V  P  R  K  D  L  S   1182

CATGTATCAAGGATTTAACGTCTCTATATGAAGCTGCTACTATTGAGGATACATGCCTTG   3720
  C  I  K  D  L  T  S  L  Y  E  A  A  T  I  E  D  T  C  L  A   1202

CATATGAACAGTTGAAAGTGGATGAAGATTCTCTATATTCATGCATTGGGGTTTCTGGTG   3780
  Y  E  Q  L  K  V  D  E  D  S  L  Y  S  C  I  G  V  S  G  A   1222

CTCAGGCTGCACAAGATATAGCAGCTCCTGTAGAAGAGGAAGAAGCAGGTGAGGGTTATC   3840
  Q  A  A  Q  D  I  A  A  P  V  E  E  E  E  A  G  E  G  Y  P   1242

CAGGGGTTCTTCCTATGGGACGAGGTTTATCTACAATGACACGGCCTACTACCTAATTTT   3900
  G  V  L  P  M  G  R  G  L  S  T  M  T  R  P  T  T  *         1259

TTTGGATGACAGGGTTGGTCTGCCCTGATTTAAGAGGAAGCCATGTCTGGAAGTTTAGTT   3960
ATACAGGTCTTGGTTCAAAGAATTGGCAGTATATGTATTACAAGAGACTGCTGGATTCAT   4020
TTAAAACATTCGAACCAGTCAGCATCCAAGCTGTTGGATCAATCCTAAGAAGTGGTTCTT   4080
GGCTTGCTATTTATTTCCTTAATGTCCATTTATGTTTAGTTGAACCACTAATAAACTATT   4140
ATCGCTGCTTATACTTTCATAGGATTAGATTATAAAAAAAATATAGCATACACTAAAGAT   4200
GTATAGGTGCCATTTTTTAATGTTGGCCATATTGTTTTGAGCAATTTTTAATGCACCCT    4260
TTAGATTTCTTAGTCATCAATTGAAATTACACATCCCCGGATTTATCAAAAAAAAAAAA   4320
AAAAAAAAAAAAAAAA                                              4337
```

Fig. 3

```
CPE       LKNGIRYLIL PNKVPPTRFE AHMEVHVGSI DEEDDEQGIA HMIEHVAFLG  247
ProtIII   LDNGMVVLLV SDPQ.AVKSL SALVVPVGSL EDPEAYQGLA HYLEHMSLMG   97
hIDE      LANGIKVLLM SDPT.TDKSS AALDVHIGSL SDPPNIAGLS HFCEHMLFLG  117
YDDC      LDNGLRYMIY PHAHPKDQVN LWLQIHTGSL QEEDNELGVA HFVEHMMFNG   85
Neu PEP   LKNGLT.VAS QYSPYAQTST VGMWIDAGSR AETDETNGTA HFLEHLAFKG   93
Rat PEP   LENGLR.VAS ENSGIS.TCT VGLWIDAGSR YENEKNNGTA HFLEHMAFKG  110

CPE       SKKR..EKLL GT........ GARSNAYTDF HHTVFHIHSP TSTKDSDDLL  287
ProtIII   SKKYPQADSL AEYLKM...H GGSHNASTAP YRTAFYLEVE ......NDAL  138
hIDE      TKKYPKENEY SQFLSE...H AGSSNAFTSG EHTNYYFDVS ......HEHL  158
YDDC      TKTWPGNKVI ETFESMGLRF GRDVNAYTSY DETVYQVSLP TTQKQN...L  132
Neu PEP   TTKRTQQQLE LEIENM.... GAHLNAYTSR ENTVYF.... ..AKALNEDV  133
Rat PEP   TKKRSQLDLE LEIENM.... GAHLNAYTSR EQTVYY.... ..AKAFSKDL  150

CPE       PSVLDALNEI TFHPNFLASR IEKERRALIS ELQMMNTIE            326
ProtIII   PGAVDRLADA IAEPLLDKKY AERERNAVNA ELTMARTRD            177
hIDE      EGALDRFAQF FLCPLFDESC KDREVNAVDS EHEKNVMND            197
YDDC      QQVMAIFSEW SNAATFEKLE VDAERGVITE EWRAHQDAK            171
Neu PEP   PKCVDILQDI LQNSKLEESA IERERDVILR ES...EEVE            169
Rat PEP   PRAVEILADI IQNSTLGEAE IERERGVILR EM...QEVE            186
```

Structure of CPP encoded by cDNA

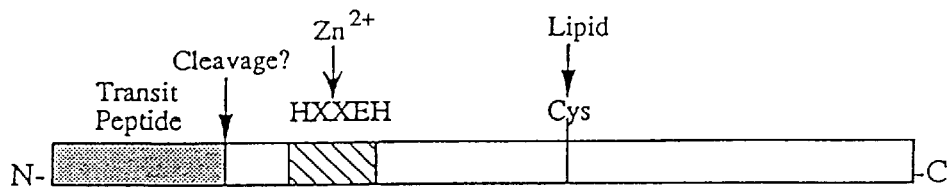

Length: 1259 amino acids

Predicted $M_r$ = 139.6 kDa

*Fig. 5*

```
  5  ASTSTSSLSVVGTNLSLPPHRHHRHFHSPSSISTRI...RTNRLFLSSSL   51
     ||.|.| :..|  . |:|       |:|..| ..|.    |:: :..|
  2  ASSSSSIFTGVKFSPILAP......FNSGDSRRSRYLKDSRNKVRFNPSS  45

52  AFSSPRDARVVHAGL....GLR..RNTPDVWKHYSSVLSQPTAPVPVRQS  95
      :  .|: .|| ::|    ||: . .|:... ||: . . |.:..
 46  PRLTPHRVRVEAPSLIPYNGLWYVSVFSFVFMETELVLGSKFC*VQLNRF  95

96  CTSCCL......ASAKKRRSNLPRFVPGAFFDSSSFGLSKDKLRHASVKR  139
     .. |.       | :....:..|.| :.:: :....: : || :.  ||
 96  VKFCVEFCGVKGAQPNSHKGRLKRNIVSG.KEATGYHFLKDVISVLLVKG  144

140  VQL..................PHATVGPDEPHAASTTWQEG.VAEKQDL  169
     :.|               .:||:|||||||||:|.|.:| |||:|||
145  IKLESEEHYLVPLWIELHLVCRGRATLGPDEPHAAGTAWPDGIVAERQDL  194

170  SLFDSELER..LEGFLGSELPSHPKLHRGQLKNGIRYLILPNKVPPTRFE  217
     .|:...|::.  ||:|||:||||||||||||||||:||||||||||.|||
195  DLLPPEIDSAELEAFLGCELPSHPKLHRGQLKNGLRYLILPNKVPPARFE  244

218  AHMEVHVGSIDEEDDEQGIAHMIEHVAFLGSKKREKLLGTGARSNAYTDF  267
     |||||||||||||:|||||||||||||||||||||||||||||||||||
245  AHMEVHVGSIDEEEDEQGIAHMIEHVAFLGSKKREKLLGTGARSNAYTDF  294

268  HHTVF  272
     |||||
295  HHTVF  299
```

*Fig. 6*

Fig. 7(A)

```
                           /Sau3AI
              NlaIII\ /DpnI                                          /Tsp45I
SEQ ID NO. 11      /BspHI                       /MaeI   /MaeIII
           ↘ GAAAACTCATGATCGCCAAGTTGAAATAGTATAGAAAGCCTAGTTTAGAGTGACAAACAA
         1 ---+---|---+---|---+---|---+---|---+---|---+---|  60
             CTTTTGAGTACTAGCGGTTCAACTTTATCATATCTTTCGGATCAAATCTCACTGTTTGTT
rf1          E N S * S P S * N S I E S L V * S D K Q
rf2           K T H D R Q V E I V * K A * F R V T N N
rf3            K L M I A K L K * Y R K P S L E * Q T T
            -----------------------------------------------------------
rf4            F S M I A L N F Y Y L F G L K S H C V
rf5           F V * S R W T S I T Y F A * N L T V F L
rf6          F E H D G L Q F L I S L R T * L S L C

/TaqI
               Sau3AI\ /DpnI
                 /ClaI /MaeIII /HphI
             CACTTGAAATCCTAAACAATCGATCTTGTAACCACTATTGCACATCACCACAAAACACAC
        61 ---+---|---+---|---+---|---+---|---+---|---+---| 120
             GTGAACTTTAGGATTTGTTAGCTAGAACATTGGTGATAACGTGTAGTGGTGTTTTGTGTG
rf1          H L K S * T I D L V T T I A H H H K T H
rf2           T * N P K Q S I L * P L L H I T T K H T
rf3            L E I L N N R S C N H Y C T S P Q N T H
            -----------------------------------------------------------
rf5          V S S I R F L R D Q L W * Q V D G C F V
rf6           V Q F G L C D I K Y G S N C M V V F C V
rf7            C K F D * V I S R T V V I A C * W L V C

/TfiI
                /AluI       /MsII /MseI                    /HinfI
             ATTATCTGACGAAAGCTAATCACATTCAAATGATTAAACCAAAATAACAGAATCTAAACA
        121 ---+---|---+---|---+---|---+---|---+---|---+---| 180
             TAATAGACTGCTTTCGATTAGTGTAAGTTTACTAATTTGGTTTTATTGTCTTAGATTTGT
rf1          I I * R K L I T F K * L N Q N N R I * T
rf2           L S D E S * S H S N D * T K I T E S K H
rf3            Y L T K A N H I Q M I K P K * Q N L N I
            -----------------------------------------------------------
rf4          C * R V F A L * M * I I L G F Y C F R F
rf5           N D S S L * D C E F S * V L I V S D L C
rf6            M I Q R F S I V N L H N F W F L L I * V
                        /PacI
           Tsp509I \ /MseI
                /MseI      BsmAI\
                /AseI      /TaqI    /BsaI                 /Tsp509I
             TTAATTAACTTATATTCGAGATACAACGAGACCTATACGAGTTTGAATGAAAGACAATTT
        181 ---+---|---+---|---+---|---+---|---+---|---+---| 240
             AATTAATTGAATATAAGCTCTATGTTGCTCTGGATATGCTCAAACTTACTTTCTGTTAAA
rf1          L I N L Y S R Y N E T Y T S L N E R Q F
rf2           * L T Y I R D T T R P I R V * M K D N F
rf3            N * L I F E I Q R D L Y E F E * K T I F
            -----------------------------------------------------------
rf4          M L * S I N S I C R S R Y S N S H F V I
rf5           * N V * I R S V V L G I R T Q I F S L K
rf6            N I L K Y E L Y L S V * V L K F S L C N
```

```
                               /RsaI Sau3A1\              /MboII
              /AccI    /Bsp14O7I          /DpnI    /AluI
              TCTTGTCTACTATATGTACAAGAAAAAATAGAGATCATACAAATAGCTTTTCTTCTAACT
         241  ---+---|---+---|---+---|---+---|---+---|---+---|  300
              AGAACAGATGATATACATGTTCTTTTTTATCTCTAGTATGTTTATCGAAAAGAAGATTGA
    rf1         S   C   L   L   Y   V   Q   E   K   I   E   I   I   Q   I   A   F   L   L   T
    rf2           L   V   Y   Y   M   Y   K   K   K   *   R   S   Y   K   *   L   F   F   *   L
    rf3             L   S   T   I   C   T   R   K   N   R   D   H   T   N   S   F   S   S   N   Y
              ------------------------------------------------------------
    rf4         K   K   D   V   I   H   V   L   F   F   L   S   *   V   F   L   K   E   E   L
    rf5           R   T   *   *   I   Y   L   F   F   Y   L   D   Y   L   Y   S   K   K   *   S
    rf6             E   Q   R   S   Y   T   C   S   F   I   S   I   M   C   I   A   K   R   R   V

/TfiI     /Tsp509I
                         Tsp509\   NlaIII\    /MseI              /NlaIII
              /TaqI    /SspI      HinfI\  DraI\   /ApoI        /MaeIII
              ATCGAAATCAATATTCTTATAATTAGGCATGAATCCTTTAAAAATTTAGGGGTCATGTAA
         301  ---+---|---+---|---+---|---+---|---+---|---+---|  360
              TAGCTTTAGTTATAAGAATATTAATCCGTACTTAGGAAATTTTTAAATCCCCAGTACATT
    rf1         I   E   I   N   I   L   I   I   R   H   E   S   F   K   N   L   G   V   M   *
    rf2           S   K   S   I   F   L   *   L   G   M   N   P   L   K   I   *   G   S   C   N
    rf3             R   N   Q   Y   S   Y   N   *   A   *   I   L   *   K   F   R   G   H   V   T
              ------------------------------------------------------------
    rf4         *   R   F   *   Y   E   *   L   *   A   H   I   R   *   F   N   L   P   *   T
    rf5           D   F   D   I   N   K   Y   N   P   M   F   G   K   F   I   *   P   D   H   L
    rf6             I   S   I   L   I   R   I   I   L   C   S   D   K   L   F   K   P   T   M   Y /Tsp509I    /TaqI
                               /NsiI   Sau3AI\                /MseI
                       /MseI        /BsmI    /MseI    /DpnI    /DraI
              CACTTAACATAAGCAAATATATGAATGCATAAAATTATTAACTTTTCGATCATTTTTTA
         361  ---+---|---+---|---+---|---+---|---+---|---+---|  420
              GTGAATTGTATTCGTTTATATACTTACGTATTTTAATAATTGAAAAGCTAGTAAAAAAT
    rf1         H   L   T   *   A   N   I   *   M   H   K   I   I   N   F   S   I   I   F   L
    rf2           T   *   H   K   Q   I   Y   E   C   I   K   L   L   T   F   R   S   F   F   *
    rf3             L   N   I   S   K   Y   M   N   A   *   N   Y   *   L   F   D   H   F   F   K
              ------------------------------------------------------------
    rf4         V   S   L   M   L   L   Y   I   F   A   Y   F   *   *   S   K   S   *   K   K
    rf5           V   *   C   L   C   I   Y   S   H   M   F   N   N   V   K   R   D   N   K   *
    rf6             C   K   V   Y   A   F   I   H   I   C   L   I   I   L   K   E   I   M   K   K /Tsp509I
                                                    /Tsp509I          /Tsp509I
                      /Tsp509I   MseI\  /DraI/ApoI    /Tsp509I
              AAAAATTATAATTTTCGGCAAACGGTATTTAAACCAAATTTCACAAAATTACATCAATTT
         421  ---+---|---+---|---+---|---+---|---+---|---+---|  480
              TTTTTAATATTAAAAGCCGTTTGCCATAAATTTGGTTTAAAGTGTTTTAATGTAGTTAAA
    rf1         K   N   Y   N   F   R   Q   T   V   F   K   P   N   F   T   K   L   H   Q   F
    rf2           K   I   I   I   F   G   K   R   Y   L   N   Q   I   S   Q   N   Y   I   N   F
    rf3             K   L   *   F   S   A   N   G   I   *   T   K   F   H   K   I   T   S   I   F
              ------------------------------------------------------------
    rf4         L   F   N   Y   N   E   A   F   P   I   *   V   L   N   *   L   I   V   D   I
    rf5           F   I   I   I   K   P   L   R   Y   K   F   W   I   E   C   F   *   M   L   K
    rf6             F   F   *   L   K   R   C   V   T   N   L   G   F   K   V   F   N   C   *   N
```

———— TO FIG. 7(C) ————

Fig. 7(c) ———TO FIG. 7(B).———

```
                    DdeI\  /BspWI
                      /BsaBI    /MseI  Tsp509I\ Sau3AI\  /DpnI
         TTTTTTTAGATTGCTATCTAAGCCCTTAACCGAAATACCTAAACCTAATTGAACCGATCA
     481 ---+---|---+---|---+---|---+---|---+---|---+---|---+---| 540
         AAAAAAATCTAACGATAGATTCGGGAATTGGCTTTATGGATTTGGATTAACTTGGCTAGT
rf1      F  F  *  I  A  I  *  A  L  N  R  N  T  *  T  *  L  N  R  S
rf2       F  F  R  L  L  S  K  P  L  T  E  I  P  K  P  N  *  T  D  Q
rf3        F  L  D  C  Y  L  S  P  *  P  K  Y  L  N  L  I  E  P  I  S
         ----------------------------------------------------------
rf4      K  K  K  S  Q  *  R  L  G  *  G  F  Y  R  F  R  I  S  G  I
rf5       K  K  L  N  S  D  L  G  K  V  S  I  G  L  G  L  Q  V  S  *
rf6        K  K  *  I  A  I  *  A  R  L  R  F  V  *  V  *  N  F  R  D

/PleI
               /Cac8I       NlaIII \    /HinfI  TaqI\
         GTTCAAAGTTGCCAGCAGATAAACAATGTTTTCATGTCCGACTCATACTCCATAGTCGAA
     541 ---+---|---+---|---+---|---+---|---+---|---+---|---+---| 600
         CAAGTTTCAACGGTCGTCTATTTGTTACAAAAGTACAGGCTGAGTATGAGGTATCAGCTT
rf1      V  Q  S  C  Q  Q  I  N  N  V  F  M  S  D  S  Y  S  I  V  E
rf2       F  K  V  A  S  R  *  T  M  F  S  C  P  T  H  T  P  *  S  N
rf3        S  K  L  P  A  D  K  Q  C  F  H  V  R  L  I  L  H  S  R  T
         ----------------------------------------------------------
rf4      L  E  F  N  G  A  S  L  C  H  K  *  T  R  S  M  S  W  L  R
rf5       N  L  T  A  L  L  Y  V  I  N  E  H  G  V  *  V  G  Y  D  F
rf6        T  *  L  Q  W  C  I  F  L  T  K  M  D  S  E  Y  E  M  T  S /HpaI
   MseI\  /HincII
       /PspI406I
       /MaeII    MboII\  /BsrI         /Eco57I          /MseI
         CGTTAACCCTGAAGAAACATATTTCCAGTGAAGGTTTAGTCTTAAATCTACCAATATAAC
     601 ---+---|---+---|---+---|---+---|---+---|---+---|---+---| 660
         GCAATTGGGACTTCTTTGTATAAAGGTCACTTCCAAATCAGAATTTAGATGGTTATATTG
rf1      R  *  P  *  R  N  I  F  P  V  K  V  *  S  *  I  Y  Q  Y  N
rf2       V  N  P  E  E  T  Y  F  Q  *  R  F  S  L  K  S  T  N  I  T
rf3        L  T  L  K  K  H  I  S  S  E  G  L  V  L  N  L  P  I  *  P
         ----------------------------------------------------------
rf4      V  N  V  R  F  F  C  I  E  L  S  P  K  T  K  F  R  G  I  Y
rf5       T  L  G  S  S  V  Y  K  W  H  L  N  L  R  L  D  V  L  I  V
rf6        R  *  G  Q  L  F  M  N  G  T  F  T  *  D  *  I  *  W  Y  L
                                                           /MseI
                                                          /HpaII
                                                         /Cfr10I
                                              DpnI\      /BsaWI
                                                  /BclI /AgeI
                                /MseI  /AciI /NlaIII
         CAGAAAAATCCAGAAAAAACTTGCCATTAACTACCGCATGATCAACCGGTTAAAACTTCT
     661 ---+---|---+---|---+---|---+---|---+---|---+---|---+---| 720
         GTCTTTTTAGGTCTTTTTTGAACGGTAATTGATGGCGTACTAGTTGGCCAATTTTGAAGA
rf1      Q  K  N  P  E  K  T  C  H  *  L  P  H  D  Q  P  V  K  T  S
rf2       R  K  I  Q  K  K  L  A  I  N  Y  R  M  I  N  R  L  K  L  L
rf3        E  K  S  R  K  N  L  P  L  T  T  A  *  S  T  G  *  N  F  W
         ----------------------------------------------------------
rf4      G  S  F  D  L  F  F  K  G  N  V  V  A  H  D  V  P  *  F  K
rf5       L  F  I  W  F  F  S  A  M  L  *  R  M  I  L  R  N  F  S  R
rf6        W  F  F  G  S  F  V  Q  W  *  S  G  C  S  *  G  T  L  V  E
```

```
                          /HphI /SspI
            GGGTGAAAATCTTTCCAAAATATTGAGATTTTGACTTCAAACCCTTTGCTACAAATAGAA
        721 ---+---|---+---|---+---|---+---|---+---|---+---| 780
            CCCACTTTTAGAAAGGTTTTATAACTCTAAAACTGAAGTTTGGGAAACGATGTTTATCTT
rf1           G * K S F Q N I E I L T S N P L L Q I E
rf2            G E N L S K I L R F * L Q T L C Y K * K
rf3             V K I F P K Y * D F D F K P F A T N R R
            ----------------------------------------------------------
rf4           Q T F I K G F Y Q S K S K L G K A V F L
rf5            P S F R E L I N L N Q S * V R Q * L Y F
rf6             P H F D K W F I S I K V E F G K S C I S

/MseI
              Tsp509I\  /MseI          /MseI           /AseI
            GGTTTGATTTTGGAATTAAAATATATAGTTTGTATTAAAAAAGAAAGAAACATTAATATA
        781 ---+---|---+---|---+---|---+---|---+---|---+---| 840
            CCAAACTAAAACCTTAATTTTATATATCAAACATAATTTTTTCTTTCTTTGTAATTATAT
rf1           G L I L E L K Y I V C I K K E R N I N I
rf2            V * F W N * N I * F V L K K K E T L I Y
rf3             F D F G I K I Y S L Y * K R K K H * Y T
            ----------------------------------------------------------
rf4           L N S K P I L I Y L K Y * F L F F C * Y
rf5            T Q N Q F * F I Y N T N F F F S V N I Y
rf6             P K I K S N F Y I T Q I L F S L F M L I

/MooII
                                                             /MaeII
                        /MseI                     /BbsI    /AluI
            CTCATATAAAAAGAGTTTAACAAAATAAAAATCAGGAAGGAGAAGACAATAAAACGTAGC
        841 ---+---|---+---|---+---|---+---|---+---|---+---| 900
            GAGTATATTTTTCTCAAATTGTTTTATTTTTAGTCCTTCCTCTTCTGTTATTTTGCATCG
rf1           L I * K E F N K I K I R K E K T I K R S
rf2            S Y K K S L T K * K S G R R R Q * N V A
rf3             H I K R V * Q N K N Q E G E D N K T * L
            ----------------------------------------------------------
rf4           V * I F L T * C F L F * S P S S L L V Y
rf5            E Y L F L K V F Y F D P L L L C Y F T A
rf6             S M Y F S N L L I F I L F S F V I F R L

/BsmBI
                              /MnII                          /BsmAI
                 /MboII/MnII/EarI          /MseI             /BseRI
            TAACCTCATCTCCCTCTTCTTTTTTTTTGTTCTTTAATAGTTTCCGTCTCTCTTTTTTC
        901 ---+---|---+---|---+---|---+---|---+---|---+---| 960
            ATTGGAGTAGAGGGAGAAGAAAAAAAAAACAAGAAATTATCAAAGGCAGAGAGAAAAAAG
rf1           * P H L P L L F F L F F N S F R L S F F
rf2            N L I S L F F F F C S L I V S V S L F S
rf3             T S S P S S F F F V L * * F P S L F F L
            ----------------------------------------------------------
rf4           S V E D G E E K K K T R * Y N G D R K K
rf5            L R M E R K K K K Q E K I T E T E R K E
rf6             * G * R G R R K K K N K L L K R R E K K
```

```
                                      MboII\           MnlI\
                /MnlI/MnlI    /MnlI       HphI\    /EarI
        TCCTCCACCTCTCCTTTGTCCTCAATAGCCGACGATGGCTTCATCGTCCTCTTCCATTTT
    961 ---+---|---+---|---+---|---+---|---+---|---+---|  1020
        AGGAGGTGGAGAGGAAACAGGAGTTATCGGCTGCTACCGAAGTAGCAGGAGAAGGTAAAA
rf1      S  S  T  S  P  L  S  S  I  A  D  D  G  F  I  V  L  F  H  F
rf2      P  P  P  L  L  C  P  Q  *  P  T [M  A  S  S  S  S  I  F  *
rf3       L  H  L  S  F  V  L  N  S  R  R  W  L  H  R  P  L  P  F  S
         -------------------------------------------------------------
rf4      R  R  W  R  E  K  T  R  L  L  R  R  H  S  *  R  G  R  G  N
rf5       G  G  G  R  R  Q  G  *  Y  G  V  I  A  E  D  D  E  E  M  K
rf6        E  E  V  E  G  K  D  E  I  A  S  S  P  K  M  T  R  K  W  K

SgrAI\  /HpaII                                        /Fnu4HI
        / CfrI0I                    HpaII\ Fnu4HI\       /BsrBI
        / BsaWI  Sau3AI\  /DpnI MseI\      /BspMII    /AciI
        /AgeI  /MseI  DdeI\   /AluI    /BsaWI    /AciI
        CACCGGTGTTAAGTTCTCTCCGATCTTAGCTCCCTTTAACTCCGGAGATAGCCGCCGCTC
   1021 ---+---|---+---|---+---|---+---|---+---|---+---|  1080
        GTGGCCACAATTCAAGAGAGGCTAGAATCGAGGGAAATTGAGGCCTCTATCGGCGGCGAG
rf1      H  R  C  *  V  L  S  D  L  S  S  L  *  L  R  R  *  P  P  L
rf2       T  G  V  K  F  S  P  I  L  A  P  F  N  S  G  D  S  R  R  S
rf3        P  V  L  S  S  L  R  S  *  L  P  L  T  P  E  I  A  A  A  L
         -------------------------------------------------------------
rf4      E  G  T  N  L  E  R  R  D  *  S  G  K  V  G  S  I  A  A  A
rf5       V  P  T  L  N  E  G  I  K  A  G  K  L  E  P  S  L  R  R  E
rf6        *  R  H  *  T  R  E  S  R  L  E  R  *  S  R  L  Y  G  G  S

/BstUI
        /TaqI                      Fnu4HI\ /BseRI /BsmBI
             /EcoRV       /HpaII   Mse\  /HgaI  /AciI   /BsmAI
        TCGATATCTAAAAGATAGCCGGAATAAAGTTAGGTTTAATCCATCGTCGCCGCGTCTCAC
   1081 ---+---|---+---|---+---|---+---|---+---|---+---|  1140
        AGCTATAGATTTTCTATCGGCCTTATTTCAATCCAAATTAGGTAGCAGCGGCGCAGAGTG
rf1      S  I  S  K  R  *  P  E  *  S  *  V  *  S  I  V  A  A  S  H
rf2       R  Y  L  K  D  S  R  N  K  V  R  F  N  P  S  S  P  R  L  T
rf3        D  I  *  K  I  A  G  I  K  L  G  L  I  H  R  R  R  V  S  L
         -------------------------------------------------------------
rf4      R  S  I  *  F  I  A  P  I  F  N  P  K  I  W  R  R  R  T  E
rf5       R  Y  R  F  S  L  R  F  L  T  L  N  L  G  D  D  G  R  R  V
rf6        E  I  D  L  L  Y  G  S  Y  L  *  T  *  D  M  T  A  A  D  *

/HgaI                                        /SnaBI
                 /TaqI      /Tsp509I              /RsaI
         MnlI\  /BstUI /AluI    /MseI      /BslI MaeII\ /BsaAI
        TCCTCATCGTGTTCGCGTCGAAGCTCCGTCTTTAATTCCCTATAATGGTCTTTGGTACGT
   1141 ---+---|---+---|---+---|---+---|---+---|---+---|  1200
        AGGAGTAGCACAAGCGCAGCTTCGAGGCAGAAATTAAGGGATATTACCAGAAACCATGCA
rf1      S  S  S  C  S  R  R  S  S  V  F  N  S  L  *  W  S  L  V  R
rf2       P  H  R  V  R  V  E  A  P  S  L  I  P  Y  N  G  L  W  Y  V
rf3        L  I  V  F  A  S  K  L  R  L  *  F  P  I  M  V  F  G  T  Y
         -------------------------------------------------------------
rf4      S  R  M  T  N  A  D  F  S  R  R  *  N  G  I  I  T  K  P  V
rf5       G  *  R  T  R  T  S  A  G  D  K  I  G  *  L  P  R  Q  Y  T
rf6        E  E  D  H  E  R  R  L  E  T  K  L  E  R  Y  H  D  K  T  R
```

```
                                   /Tsp5091         /Tsp5091
              /AluI      /NlaIII  /XmnI      /ApoI
         ATCAGTTTTCAGCTTCGTGTTCATGGAAACTGAATTAGTTCTTGGTTCAAAATTTTGTTG
    1201 ---+---|---+---|---+---|---+---|---+---|---+---| 1260
         TAGTCAAAAGTCGAAGCACAAGTACCTTTGACTTAATCAAGAACCAAGTTTTAAAACAAC
rf1       I  S  F  Q  L  R  V  H  G  N  *  I  S  S  W  F  K  I  L  L
rf2        S  V  F  S  F  V  F  M  E  T  E  L  V  L  G  S  K  F  C  *
rf3         Q  F  S  A  S  C  S  W  K  L  N  *  F  L  V  Q  N  F  V  E
         ----------------------------------------------------------------
rf4       Y  *  N  E  A  E  H  E  H  F  S  F  *  N  K  T  *  F  K  T
rf5        D  T  K  L  K  T  N  M  S  V  S  N  T  R  P  E  F  N  Q  Q
rf6         I  L  K  *  S  R  T  *  P  F  Q  I  L  E  Q  N  L  I  K  N
                                                                /HhaI
                                                          HhaI\  /Fnu4HI
                          /Tsp5091                              / Cac8I
                   /TaqI   /MseI        /Tsp5091       /MseI   / BstUI
            MseI\   /ClaI  /ApoI         /ApoI     BssHII\
         AGTTCAGTTAAATCGATTTGTTAAATTTTGTGTTGAATTTTGTGGTGTTAAGGGCGCGCA
    1261 ---+---|---+---|---+---|---+---|---+---|---+---| 1320
         TCAAGTCAATTTAGCTAAACAATTTAAAACACAACTTAAAACACCACAATTCCCGCGCGT
rf1       S  S  V  K  S  I  C  *  I  L  C  *  I  L  W  C  *  G  R  A
rf2        V  Q  L  N  R  F  V  K  F  C  V  E  F  C  G  V  K  G  A  Q
rf3         F  S  *  I  D  L  L  N  F  V  L  N  F  V  V  L  R  A  R  S
         ----------------------------------------------------------------
rf4       S  N  L  *  I  S  K  N  F  K  T  N  F  K  T  T  N  L  A  R
rf5        T  *  N  F  R  N  T  L  N  Q  T  S  N  Q  P  T  L  P  A  C
rf6         L  E  T  L  D  I  Q  *  I  K  H  Q  I  K  H  H  *  P  R  A

/Tsp5091        /MnlI                         /HpaII
                 /BspWI   /MaeII                              /BsaWI
           BsmFI\  /ApoI /BbvI MseI\ /DraI           /AluI
         GCCAAATTCGCATAAGGGACGTTTAAAGAGGAACATTGTTTCGGGAAAAGAAGCTACCGG
    1321 ---+---|---+---|---+---|---+---|---+---|---+---| 1380
         CGGTTTAAGCGTATTCCCTGCAAATTCTCCTTGTAACAAAGCCCTTTTCTTCGATGGCC
rf1       A  K  F  A  *  G  T  F  K  E  E  H  C  F  G  K  R  S  Y  R
rf2        P  N  S  H  K  G  R  L  K  R  N  I  V  S  G  K  E  A  T  G
rf3         Q  I  R  I  R  D  V  *  R  G  T  L  F  R  E  K  K  L  P  D
         ----------------------------------------------------------------
rf4       L  W  I  R  M  L  S  T  *  L  P  V  N  N  R  S  F  F  S  G
rf5        G  F  E  C  L  P  R  K  F  L  F  M  T  E  P  F  S  A  V  P
rf6         A  L  N  A  Y  P  V  N  L  S  S  C  Q  K  P  F  L  L  *  R

TfiI \ /SapI
                           /Tsp5091       TfiI \  HinfI \ /EarI
             /EcoRV         /MaeII               /HinfI /AluI
         ATATCACTTTCTCAAGGACGTAATTTCTGTCTTACTTGTAAAAGGAATCAAGCTGGAATC
    1381 ---+---|---+---|---+---|---+---|---+---|---+---| 1440
         TATAGTGAAAGAGTTCCTGCATTAAAGACAGAATGAACATTTTCCTTAGTTCGACCTTAG
rf1       I  S  L  S  Q  G  R  N  F  C  L  T  C  K  R  N  Q  A  G  I
rf2        Y  H  F  L  K  D  V  I  S  V  L  L  V  K  G  I  K  L  E  S
rf3         I  T  F  S  R  T  *  F  L  S  Y  L  *  K  E  S  S  W  N  Q
         ----------------------------------------------------------------
rf4       S  I  V  K  E  L  V  Y  N  R  D  *  K  Y  F  S  D  L  Q  F
rf5        Y  *  K  R  L  S  T  I  E  T  K  S  T  F  P  I  L  S  S  D
rf6         I  D  S  E  *  P  R  L  K  Q  R  V  Q  L  L  F  *  A  P  I
```

```
                        /MboII                                      /TaqI
                  /MaeI                        /MnlI/TaqI    /MboII
          AGAAGAGCATTACCTAGTGCCTTTGTGGATAGAACTGCATTTAGTTTGTCGAGGTCGAGT
    1441  ---+---|---+---|---+---|---+---|---+---|---+---|  1500
          TCTTCTCGTAATGGATCACGGAAACACCTATCTTGACGTAAATCAAACAGCTCCAGCTCA
rf1        R  R  A  L  P  S  A  F  V  D  R  T  A  F  S  L  S  R  S  S
rf2         E  E  H  Y  L  V  P  L  W  I  E  L  H  L  V  C  R  G  R  V
rf3          K  S  I  T  *  C  L  C  G  *  N  C  I  *  F  V  E  V  E  F
          ------------------------------------------------------------
rf4        *  F  L  M  V  *  H  R  Q  P  Y  F  Q  M  *  N  T  S  T  S
rf5         S  S  C  *  R  T  G  K  H  I  S  S  C  K  T  Q  R  P  R  T
rf6          L  L  A  N  G  L  A  K  T  S  L  V  A  N  L  K  D  L  D  L

/AluI
          TTGACATCTTCTCTGGTAAGTAAGCTACATCATTTACTTTCTATGTTCTTGTCTTGTGCT
    1501  ---+---|---+---|---+---|---+---|---+---|---+---|  1560
          AACTGTAGAAGAGACCATTCATTCGATGTAGTAAATGAAAGATACAAGAACAGAACACGA
rf1        L  T  S  S  L  V  S  K  L  H  H  L  L  S  M  F  L  S  C  A
rf2         *  H  L  L  W  *  V  S  Y  I  I  Y  F  L  C  S  C  L  V  L
rf3          D  I  F  S  G  K  *  A  T  S  F  T  F  Y  V  L  V  L  C  L
          ------------------------------------------------------------
rf4        N  S  M  K  E  P  L  Y  A  V  D  N  V  K  *  T  R  T  K  H
rf5         Q  C  R  R  Q  Y  T  L  *  M  M  *  K  R  H  E  Q  R  T  S
rf6          K  V  D  E  R  T  L  L  S  C  *  K  S  E  I  N  K  D  Q  A

/PleI       /NspI
                 HpaI\       /HinfI /NlaIII           /SfaNI
                   MseI\ /HincII   /AflIII         /DdeI/BsgI
          TGTTTGATTTATCTCTGTTAACTGACTCAACATGTGCAGAGAAACATTCTCAGATTGTGA
    1561  ---+---|---+---|---+---|---+---|---+---|---+---|  1620
          ACAAACTAAATAGAGACAATTGACTGAGTTGTACACGTCTCTTTGTAAGAGTCTAACACT
rf1        C  L  I  Y  L  C  *  L  T  Q  H  V  Q  R  N  I  L  R  L  *
rf2         V  *  F  I  S  V  N  *  L  N  M  C  R  E  T  F  S  D  C  D
rf3          F  D  L  S  L  L  T  D  S  T  C  A  E  K  H  S  Q  I  V  M
          ------------------------------------------------------------
rf4        K  N  S  K  D  R  N  V  S  E  V  H  A  S  F  C  E  *  I  T
rf5         T  Q  N  I  E  T  L  Q  S  L  M  H  L  S  V  N  E  S  Q  S
rf6          Q  K  I  *  R  Q  *  S  V  *  C  T  C  L  F  M  R  L  N  H /NspI /RsaI
             Sau96I\     /BbvI      /NlaIII        /HaeIII
                  /AvaII  Fnu4HI\ BspWI\   /AluI
          TGCAACTCTTGGACCAGATGAGCCACATGCTGCTGGTACAGCTTGGCCTGATGGTATTGT
    1621  ---+---|---+---|---+---|---+---|---+---|---+---|  1680
          ACGTTGAGAACCTGGTCTACTCGGTGTACGACGACCATGTCGAACCGGACTACCATAACA
rf1        C  N  S  W  T  R  *  A  T  C  C  W  Y  S  L  A  *  W  Y  C
rf2         A  T  L  G  P  D  E  P  H  A  A  G  T  A  W  P  D  G  I  V
rf3          Q  L  L  D  Q  M  S  H  M  L  L  V  Q  L  G  L  M  V  L  L
          ------------------------------------------------------------
rf4        I  C  S  K  S  W  I  L  W  M  S  S  T  C  S  P  R  I  T  N
rf5         A  V  R  P  G  S  S  G  C  A  A  P  V  A  Q  G  S  P  I  T
rf6          H  L  E  Q  V  L  H  A  V  H  Q  Q  Y  L  K  A  Q  H  Y  Q
```

```
                                              /TaqI
                         Sau3AI\   /DpnI
                                /BstYI                                    /MaeI
         BsmAI\  /AciI     /BglII          /Dde /MnlI         /AluI
                 TGCGGAGAGACAAGATCTCGACTTATTGCCTCCTGAGATTGATAGTGCAGAGCTAGAAGC
         1681 ---+---|---+---|---+---|---+---|---+---|---+---|---+---| 1740
                 ACGCCTCTCTGTTCTAGAGCTGAATAACGGAGGACTCTAACTATCACGTCTCGATCTTCG
    rf1        C  G  E  T  R  S  R  L  I  A  S  *  D  *  *  C  R  A  R  S
    rf2          A  E  R  Q  D  L  D  L  L  P  P  E  I  D  S  A  E  L  E  A
    rf3            R  R  D  K  I  S  T  Y  C  L  L  R  L  I  V  Q  S  *  K  R
         -----------------------------------------------------------------
    rf4        N  R  L  S  L  I  E  V  *  Q  R  R  L  N  I  T  C  L  *  F
    rf5          A  S  L  C  S  R  S  K  N  G  G  S  I  S  L  A  S  S  S  A
    rf6            Q  P  S  V  L  D  R  S  I  A  E  Q  S  Q  Y  H  L  A  L  L
                                                         /ScrFI
                                                         /NciI
                            /BsgI                        /HpaII /Tsp509I
                   /XmnI      /FokI                      /BsaJI /MunI
                 GTTTCTTGGTTGTGAACTTCCTTCTCATCCAAAGTTGCACCGGGGTCAATTGAAAAATGG
         1741 ---+---|---+---|---+---|---+---|---+---|---+---| 1800
                 CAAAGAACCAACACTTGAAGGAAGAGTAGGTTTCAACGTGGCCCCAGTTAACTTTTTACC
    rf1        V  S  W  L  *  T  S  F  S  S  K  V  A  P  G  S  I  E  K  W
    rf2          F  L  G  C  E  L  P  S  H  P  K  L  H  R  G  Q  L  K  N  G
    rf3            F  L  V  V  N  F  L  L  I  Q  S  C  T  G  V  N  *  K  M  G
         -----------------------------------------------------------------
    rf4        R  K  K  T  T  F  K  R  R  M  W  L  Q  V  P  T  L  Q  F  I
    rf5          N  R  P  Q  S  S  G  E  *  G  F  N  C  R  P  *  N  F  F  P
    rf6            T  E  Q  N  H  V  E  K  E  D  L  T  A  G  P  D  I  S  F  H

TaqI\    /EcoRV                                  /Tsp509I
                 GCTTCGATATCTTATTTTGCCAAACAAAGTTCCACCGAACAGGTAAATTGAGTAGAATGC
         1801 ---+---|---+---|---+---|---+---|---+---|---+---| 1860
                 CGAAGCTATAGAATAAAACGGTTTGTTTCAAGGTGGCTTGTCCATTTAACTCATCTTACG
    rf1        A  S  I  S  Y  F  A  K  Q  S  S  T  E  Q  V  N  *  V  E  C
    rf2          L  R  Y  L  I  L  P  N  K  V  P  P  N  R  *  I  E  *  N  A
    rf3            F  D  I  L  F  C  Q  T  K  F  H  R  T  G  K  L  S  R  M  L
         -----------------------------------------------------------------
    rf4        P  K  S  I  K  N  Q  W  V  F  N  W  R  V  P  L  N  L  L  I
    rf5          S  R  Y  R  I  K  G  F  L  T  G  G  F  L  Y  I  S  Y  F  A
    rf6            A  E  I  D  *  K  A  L  C  L  E  V  S  C  T  F  Q  T  S  H
                                                                  /HpaII
                                                                  /CfrlOI
                 /TaqI                                            /BsaWI
                   /BsmI    /AccI         /MseI                   /AgeI
                 TCGAAGTTGGTCTACTTGTGATACTCTTAATGACAATATATCATTCCTTGAAAACCGGTA
         1861 ---+---|---+---|---+---|---+---|---+---|---+---| 1920
                 AGCTTCAACCAGATGAACACTATGAGAATTACTGTTATATAGTAAGGAACTTTTGGCCAT
    rf1        S  K  L  V  Y  L  *  Y  S  *  *  Q  Y  I  I  P  *  K  P  V
    rf2          R  S  W  S  T  C  D  T  L  N  D  N  I  S  F  L  E  N  R  *
    rf3            E  V  G  L  L  V  I  L  L  M  T  I  Y  H  S  L  K  T  G  K
         -----------------------------------------------------------------
    rf4        S  S  T  P  R  S  T  I  S  K  I  V  I  Y  *  E  K  F  V  P
    rf5          R  L  Q  D  V  Q  S  V  R  L  S  L  I  D  N  R  S  F  R  Y
    rf6            E  F  N  T  *  K  H  Y  E  *  H  C  Y  I  M  G  Q  F  G  T
```

———— TO FIG. 7(I) ————

Fig. 7(I) ———TO FIG. 7(H)———

```
                                      /TfiI/MseI
                                   /PflMI/MboII
                              /MseI/NdeI  /HinfI
                            /AluI BslI\  BbsI\ /AflII
          AGCAAAATGGTTATAGCTTAACCATATGGTGGAATCCTTAAGGTCTTCCTGCTATATCTT
     1921 ---+---|---+---|---+---|---+---|---+---|---+---|  1980
          TCGTTTTACCAATATCGAATTGGTATACCACCTTAGGAATTCCAGAAGGACGATATAGAA
rf1        S  K  M  V  I  A  *  P  Y  G  G  I  L  K  V  F  L  L  Y  L
rf2         A  K  W  L  *  L  N  H  M  V  E  S  L  R  S  S  C  Y  I  L
rf3          Q  N  G  Y  S  L  T  I  W  W  N  P  *  G  L  P  A  I  S  Y
          ----------------------------------------------------------
rf4        L  C  F  P  *  L  K  V  M  H  H  F  G  *  P  R  G  A  I  D
rf5         A  F  H  N  Y  S  L  W  I  T  S  D  K  L  D  E  Q  *  I  K
rf6          L  L  I  T  I  A  *  G  Y  P  P  I  R  L  T  K  R  S  Y  R Sau3AI\
                            /MnlI                    NlaIII\
                            /MaeI                    /NlaIII
          ATTTGAGTTTGGAAATGTTTTCAATGCTAGATTTGAGGCACACATGGAAGTTCATGTAGG
     1981 ---+---|---+---|---+---|---+---|---+---|---+---|  2040
          TAAACTCAAACCTTTACAAAAGTTACGATCTAAACTCCGTGTGTACCTTCAAGTACATCC
rf1        I  *  V  W  K  C  F  Q  C  *  I  *  G  T  H  G  S  S  C  R
rf2         F  E  F  G  N  V  F  N  A  R  F  E  A  H  M  E  V  H  V  G
rf3          L  S  L  E  M  F  S  M  L  D  L  R  H  T  W  K  F  M  *  D
          ----------------------------------------------------------
rf4        *  K  L  K  S  I  N  E  I  S  S  K  L  C  V  H  F  N  M  Y
rf5         N  S  N  P  F  T  K  L  A  L  N  S  A  C  M  S  T  *  T  P
rf6          I  Q  T  Q  F  H  K  *  H  *  I  Q  P  V  C  P  L  E  H  L /  TaqI
             /MnlI
             /DpnI                                        /NspI
             |    /AlwI         /MboII              /NdeI /NlaIII
          ClaI\   /AlwI      /MboII      /NdeI     /AflIII
          ATCGATTGATGAGGAAGAAGATGAGCAAGGGATTGCTCATATGATAGAACATGTTGCTTT
     2041 ---+---|---+---|---+---|---+---|---+---|---+---|  2100
          TAGCTAACTACTCCTTCTTCTACTCGTTCCCTAACGAGTATACTATCTTGTACAACGAAA
rf1        I  D  *  *  G  R  R  *  A  R  D  C  S  Y  D  R  T  C  C  F
rf2         S  I  D  E  E  E  D  E  Q  G  I  A  H  M  I  E  H  V  A  F
rf3          R  L  M  R  K  K  M  S  K  G  L  L  I  *  *  N  M  L  L  S
          ----------------------------------------------------------
rf4        S  R  N  I  L  F  F  I  L  L  P  N  S  M  H  Y  F  M  N  S
rf5         D  I  S  S  S  S  S  S  C  P  I  A  *  I  I  S  C  T  A  K
rf6          I  S  Q  H  P  L  L  H  A  L  S  Q  E  Y  S  L  V  H  Q  K RsaI\ Cac8I\   /BsrBI
                    /StyI           NlaIV\  /Bsp1286I
                    /BsaJI    /MaeII    BanI\   /AciI
          CCTTGGGAGCAAGAAACGTGAGAAACTTCTTGGTACAGGTGCCCGCTCTAATGCCTACAC
     2101 ---+---|---+---|---+---|---+---|---+---|---+---|  2160
          GGAACCCTCGTTCTTTGCACTCTTTGAAGAACCATGTCCACGGGCGAGATTACGGATGTG
rf1        P  W  E  Q  E  T  *  E  T  S  W  Y  R  C  P  L  *  C  L  H
rf2         L  G  S  K  K  R  E  K  L  L  G  T  G  A  R  S  N  A  Y  T
rf3          L  G  A  R  N  V  R  N  F  L  V  Q  V  P  A  L  M  P  T  P
          ----------------------------------------------------------
rf4        E  K  P  A  L  F  T  L  F  K  K  T  C  T  G  A  R  I  G  V
rf5         R  P  L  L  F  R  S  F  S  R  P  V  P  A  R  E  L  A  *  V
rf6          G  Q  S  C  S  V  H  S  V  E  Q  Y  L  H  G  S  *  H  R  C
```

```
                                                            /MboII
                                              /BsII
             CGATTTCCACCATACAGTATTTATATTCATTCTCCAACCCACACGAAGGTTTGTTCTCTT
        2161 ---+---|---+---|---+---|---+---|---+---|---+---| 2220
             GCTAAAGGTGGTATGTAATAAATATAAGTAAGAGGTTGGGTGTGCTTCCAAACAAGAGAA
   rf1         R  F  P  P  Y  S  I  Y  I  H  S  P  T  H  T  K  V  C  S  L
   rf2          D  F  H  H  T  V  F  I  F  I  L  Q  P  T  R  R  F  V  L  F
   rf3            I  S  T  I  Q  Y  L  Y  S  F  S  N  P  H  E  G  L  F  S  S
             ------------------------------------------------------------
   rf4         G  I  E  V  M  C  Y  K  Y  E  N  E  L  G  C  S  P  K  N  E
   rf5          S  K  W  W  V  T  N  I  N  M  R  W  G  V  R  L  N  T  R  K
   rf6            R  N  G  G  Y  L  I  *  I  *  E  G  V  W  V  F  T  Q  E  R

/EarI                                         /Tsp509I
             CTACACCTATTGGCGTATTTAGTGATGTATCTTTTTCTTGGTTAGTTCAATTCACAGGTT
        2221 ---+---|---+---|---+---|---+---|---+---|---+---| 2280
             GATGTGGATAACCGCATAAATCACTACATAGAAAAAGAACCAATCAAGTTAAGTGTCCAA
   rf1         L  H  L  L  A  Y  L  V  M  Y  L  F  L  G  *  F  N  S  Q  V
   rf2          Y  T  Y  W  R  I  *  *  C  I  F  F  L  V  S  S  I  H  R  F
   rf3            T  P  I  G  V  F  S  D  V  S  F  S  W  L  V  Q  F  T  G  F
             ------------------------------------------------------------
   rf4         E  V  G  I  P  T  N  L  S  T  D  K  E  Q  N  T  *  N  V  P
   rf5          *  V  *  Q  R  I  *  H  H  I  K  K  K  T  L  E  I  *  L  N
   rf6            R  C  R  N  A  Y  K  T  I  Y  R  K  R  P  *  N  L  E  C  T

/MseI
                                   /MnlI
             TTTATTGCCTCGTATTTACTTTAACAAATATGGTGTTTATAGTCTATATCTATATGTTGCA
        2281 ---+---|---+---|---+---|---+---|---+---|---+---|- 2341
             AAATAACGGAGCATAAATGAAATTGTTTATACCACAAATATCAGATATAGATATACAACGT
   rf1         F  I  A  S  Y  L  L  *  Q  I  W  C  L  *  S  I  S  I  C  C
   rf2          L  L  P  R  I  Y  F  N  K  Y  G  V  Y  S  L  Y  L  Y  V  A
   rf3            Y  C  L  V  F  T  L  T  N  M  V  F  I  V  Y  I  Y  M  L
             ------------------------------------------------------------
   rf4         K  *  Q  R  T  N  V  K  V  F  I  T  N  I  T  *  I  *  I  N  C
   rf5          K  N  G  R  I  *  K  L  L  Y  P  T  *  L  R  Y  R  Y  T  A
   rf6            K  I  A  E  Y  K  S  *  C  I  H  H  K  Y  D  I  D  I  H  Q
```

PLASTID PROTEOLYTIC PROCESSING ENZYME THAT CLEAVES PRECURSOR POLYPEPTIDES

This application claims priority to a provisional application filed Aug. 1, 1995 bearing Ser. No. 60/001,746, with Lamppa as the inventor.

This application is a division of application Ser. No. 08/695,177, filed Aug. 1, 1996.

The U.S. government may have rights to this invention based on support by NIH Grant GM 36419 and NSF Grant MCB 9407739.

BACKGROUND

The present invention relates to soluble plastid processing enzymes. In particular, the present invention relates to a chloroplast processing enzyme (CPE), that is an endoprotease with unique cleavage capabilities, a cDNA encoding the enzyme, and the use of the enzyme in preparing biologically active (native) polypeptides for various applications.

Enzymes (e.g. proteases) are valuable tools for use in the production of peptides and polypeptides. However, many of the known proteases cleave at so many sites in a molecule that the resultant products are not biologically active, and/or the enzymes cleave at common sites so that there is no cleavage product specificity. Specialized enzymes such as those that convert biologically inactive precursor molecules to active molecules by retaining specific portions of the molecule, would be assets to protein production, because their products could be predictable, and biologically active. Although some of these processing enzymes are known, difficulties in producing them in quantities suitable for commercial use, seriously limit their use. Some difficulties arise from problems in isolating and purifying the enzymes, other difficulties stem from the source material—many are obtained from animals which are a less desirable source than plants.

In plants, certain systems are advantageous as a source of enzymes because they produce products of general importance. For example, the chloroplast serves as the site for many biosynthetic pathways such as fatty acid synthesis, terpene synthesis, aromatic and branched amino acid synthesis, starch accumulation, nitrogen and sulfur reduction, photosynthesis, ATP generation, and carbondioxide fixation. Therefore, methods and compositions in the chloroplast are broadly applicable to non-chloroplast applications. For example, terpenes are compounds that were originally isolated from the oil of turpentine in the early days of organic chemistry. Terpene derivatives, including alcohols, aldehydes, and esters are referred to as terpenoids. Terpenoids are a category of chemicals responsible for the aromatic characteristics of fragrances. The terpenoid molecular structure is based on five-carbon units. Different chemical arrangements of the basic five-carbon units produce terpenoid compounds with different scents, such as lemongrass, lavender, menthol, jasmine, violet, and camphor. Methods and compositions from chloroplasts may be applied to the perfume industry by producing terpenoids in a manner suitable for commercial use.

Chloroplast biogenesis depends upon the import of many diverse proteins, which are synthesized in the cytoplasm as pre-proteins with N-terminal transit peptides. The transit peptide mediates pre-protein recognition by receptors on the chloroplast envelope (Schnell et al., 1994; Hirsch (et al., 1994). Upon membrane translocation into the stroma, the transit peptide is proteolytically removed, yielding a mature protein (Abad et al., 1989; Robinson et al., 1984). It has been suggested that a general stromal processing peptidase (SPP) located within the chloroplast, exhibiting the properties of a metalloprotease, cleaves the transit peptides from the diverse group of pre-proteins that are imported into the chloroplast (Abad et al., 1989; Robinson et al., 1984).

Proteins targeted to the thylakoid lumen have a bipartite transit peptide that is cleaved first by SPP, then by a thylakoid protease (Bassham et al., 1991; Kirwin et al., 1988; Konishi et al., 1993). SPP thus plays a key role in the maturation process of proteins targeted to the chloroplast. Identification and characterization of genes encoding processing proteases (peptidases) may facilitate the development of recombinant expression systems that require expression of pre-proteins and subsequent processing to remove transit peptides or other segments of the sequence that must be removed in order to yield mature proteins.

SUMMARY

A new soluble plastid processing enzyme that is an endopeptidase with unique cleavage capabilities, is purified and characterized. Isolation of the cDNA encoding the enzyme provided the deduced amino acid sequence and allows production of the enzyme by recombinant technology permitting suitable amounts to be recovered for commercial use. The enzyme cleaves transit peptides from pre-proteins that are targeted to the chloroplast. The enzyme is useful to produce mature, active proteins, for example directly in vitro or as encoded by a cDNA recombinant expression system that requires enzymatic digestion of transit peptides from pre-proteins. Unlike many known proteases, the enzyme of the present invention has substrate specificity that is limited. Consequently, the digestion does not destroy the protein as would cleavage at multiple sites. Nor are the cleavage sites common—rather they are restricted to the junction of the transit peptide and the biologically active sequence.

The plastid proteolytic processing enzyme (a form of which is a chloroplast processing enzyme, CPE) has been identified in pea (Pisum, a representative of the dicots), wheat (a monocot), and Arabidopsis, an oilseed plant which is used as a model for genetic analyses. A CPE genomic clone has been isolated from Arabidopsis A cDNA is isolated from pea. Thus, the promoter elements that direct expression of CPE genes are determined and utilized to direct expression of other genes required for useful biosynthetic pathways early during plant development.

The enzyme of the present invention belongs to a metalloendopeptidase family of enzymes. The amino acid sequence deduced from the cDNA revealed a zinc-binding motif (His—Xaa—Xaa—Glu—His) (SEQ ID NO:2) that is likely a catalytic site. The determinants for substrate specificity appear to lie outside of this domain. The sequence of CPE shows strong conservation with insulin-degrading enzyme (IDE) (25–30% at the N-terminus) and protease III. Mutational analyses of IDE and protease III indicate a role for the HXXEH motif (SEQ ID NO:2) in protein cleavage. Thus, it is likely that the HXXEH domain near the N-terminus of CPE plays a similar catalytic role in the maturation of chloroplast pre-proteins. Due to the diversity of substrates recognized and cleaved by members of this metalloendopeptidase family, it is expected that the determinants for substrate specificity reside in novel regions outside of the HXXEH domain. Most proteins targeted to the chloroplast are synthesized as precursors that are cleaved by CPE to their mature active form. In many cases the site of cleavage is unknown. Recombinant CPE produced in host cells is useful to cleave precursor polypeptides to determine the cleavage site by analyzing the cleavage products. Additionally, expression systems that rely on overexpression of CPE as well as overexpression of a pre-protein, when targeted to the chloroplast and processed, yield amounts of mature proteins suitable for commercial use.

Specific inhibitors of the plastid proteolytic processing enzyme or antisense molecules directed against cDNA or RNA producing the enzyme allow selective inactivation. Additionally, selective inactivation may be accomplished through enzyme overexpression. If different plant species respond to different inhibitors, inactivation of the plastid processing enzyme to produce a lethal phenotype, may be an effective method of eliminating undesirable plant species in the field. Therefore, specific inhibitors of CPE that allow for selective inactivation of the enzyme act as "herbicides".

Purification and isolation of naturally occurring plastid proteolytic enzymes directly from source material, such as processing CPE from chloroplasts is difficult, time consuming, and gives low yield. An alternative to the tedious process of isolating chloroplasts and purifying plastid proteolytic processing enzymes is to utilize recombinant technology to overexpress the cDNA encoding for the enzyme. Recombinant technology is a means to employ the compositions of the present invention to facilitate the production and recovery of commercially significant amounts of enzyme.

BRIEF DESCRIPTION OF THE DRAWINGS

FIG. 1. Comparison of the proteins detected by antisera raised to the 145/143 kDa doublet and to the GST-fusion protein. A soluble chloroplast extract (20 ug protein, lanes 1) and the GST-fusion protein (200 ug protein, lanes 2) were separated by SDS-PAGE, transferred to nitrocellulose, and incubated with either rabbit anti-145/143 kDa serum (1:2500 dilution; panel A) or anti-GST fusion serum (1:2500 dilution; panel B), followed by anti-rabbit IgGs conjugated with alkaline phosphatase and developed with 5-bromo-4chloro-3-indoyl phosphate and nitroblue tetrazolium.

FIG. 2. Nucleotide sequence (SEQ ID NO:1) of a cDNA coding for CPE in pea and its deduced amino acid sequence. Sequences complimentary to primers used for 5'-RACE PCR are underlined with a broken line. Amino acid sequence (SEQ ID NO:12) from tryptic peptide sequencing of the 145/143 kDa proteins is underlined with a solid line and the zinc-binding HXXEH motif is underlined twice.

FIG. 3. Comparison of the region containing the HXXEH motif of CPE (SEQ ID NO:3) with representative members of the pitrilysin family. The alignment was created using the programs PILEUP and PRETTY from the Genetics Computer Group. Residues that are identical or conservative changes (D and E; I, L and V; R and K) with those in CPE are in bold. Sequences aligned are Prot III (SEQ ID NO:4) (protease III) (Finch, et al., 1986); hIDE (SEQ ID NO:5) (human insulin-degrading enzyme) (Affholter et al., 1988); YDDC (SEQ ID NO:6) (Swiss protein P31828); NeuPEP (SEQ ID NO:7) and RatPEP (SEQ ID NO:8) (MPP b subunit from *Neurospora crassa* (Hawlitschek et al., 1988) and rat (Paces et al., 1993), respectively). The numbers at the right indicate the amino acid position in each protein.

FIG. 4. Analysis of CPE expression in light- vs. dark-grown leaves, greening leaves, and roots. (A) CPE mRNA detected by Northern analysis. 10 ug of poly$(A)^+$ RNA from light- (lane 1) or dark-grown (lane 2) leaves was separated by denaturing gel electrophoresis (1% agarose), transferred to nylon membrane and hybridized with a digoxigenin-labeled cDNA probe spanning nucleotides 1289–1790 as shown in FIG. 2. The arrow indicates the position of 25S ribosomal RNA (~4.0 kb). (B) Immunoblot of protein using the anti-GST fusion serum. Equivalent amounts of plastid protein (25 ug) from plants grown on a 16:8 h light:dark cycle (lane 1), in the dark (lane 2) or greened for 6 h (lane 3) or 24 h (lane 4) were run on a 10% acrylamide gel, transferred to nitrocellulose, incubated with the anti-GST fusion serum and detected as described in FIG. 1, legend. Protein (75 ug) from isolated root plastids were also examined (lane 5). Lane 5 was developed until the reaction was to completion. (C) Detection of CPE activity using the organelle-free assay. Plastid extracts (25 ug of protein for lanes 2–6, 50 ug for lane 7) were incubated with $^{35}$-S-met-preLHCP synthesized in *E. coli*. Lane 1 shows a mock reaction with no extract. Extracts were prepared from plants grown on the normal light:dark cycle (lane 2), in the dark (lane 3) or greened for 6 h (lane 4) or 24 h (lane 5). In a separate experiment, CPE activity was assayed from plants grown on a normal light:dark cycle (lane 6) and from roots of these plants (lane 7).

FIG. 5. Schematic structure of the cDNA encoded CPE isolated from pea. The transit peptide is shown, as is the cleavage site, the zinc binding motif (SEQ ID NO:2) that identifies this family of endopeptidases, and a potential lipid binding site that may be important for localization and/or activity in the plastid.

FIG. 6. Alignment of pea and Arabidopsis CPE open reading frames of the plastid processing endopeptidase. Only the N terminus is shown. The upper sequence is from pea (SEQ ID NO:9), and the lower sequence is from Arabidopsis (SEQ ID NO:10). The vertical lines indicate sequence identity. The small arrow points to the start of sequence similarity, suggesting the start of the mature, functional protein. The transit peptide is located upstream of this region.

FIG. 7A–J. Promoter region, transit peptide and N-terminal DNA sequence of CPE from Arabidopsis. A genomic clone was isolated using the pea cDNA for CPE as a probe. This clone, called 9A, contained a 3.5 kb insert, of which 2.3 kb has been sequenced (SEQ ID NO:11). The open reading frame (the rf2 line shows the correctly deduced sequence) can be aligned with the pea CPE (SEQ ID NO:9), but introns are also present. The start of the open reading frame is indicated with an asterisk at position 994 bp, and the zinc-binding site is underlined (at 2076 bp).

DETAILED DESCRIPTION OF THE PREFERRED EMBODIMENT

Nuclear-encoded proteins targeted to the chloroplast are typically synthesized with N-terminal transit peptides that are proteolytically removed upon import. The endopeptidases used to cleave off the transit peptide are designated "plastid processing enzymes." Structurally related proteins of 145 and 143 kDa co-purify with the soluble chloroplast processing enzyme (CPE) that cleaves the precursor for the major light harvesting chlorophyll a/b binding protein (Oblong et al., 1992). These cleaving proteins have been implicated in the maturation of the small subunit of ribulose-1,5-bisphosphate carboxylase/oxygenase (Rubisco) and acyl carrier protein (ACP).

An embodiment of a plastid processing enzyme is a soluble chloroplast processing enzyme (CPE). CPE has characteristics of a general stromal processing peptidase (SPP) and cleaves the precursor for the major light-harvesting chlorophyll a/b binding protein (LHCP). Antigenically-related proteins of 145 and 143 kDa isolated from pea co-purify with this cleavage activity.

Antibodies raised against the 145/143 kDa proteins that co-purify with the enzymatic cleavage activity have also been used to establish the presence of CPE in wheat and Arabidopsis. Furthermore, genomic clones for the enzyme with 5' and 3' flanking sequences have been isolated from Arabidopsis. These genomic clones carry the key information for turning on CPE during plastid biogenesis, and thus may respond to novel developmental signals—some of the very earliest upon fertilization.

Immunodepletion experiments were conducted in which antibodies directed against the 145/143 kDa doublet were added to an in vitro cleavage assay. The immunodepletion studies show that the 145/143 kDa doublet is indeed required for cleavage of the LHCP precursor (preLHCP), and indicate that these proteins are involved in the removal of the transit peptides of the small subunit of ribulose-1,5-bisphosphate carboxylase/oxygenase (Rubisco) and the acyl carrier protein (ACP).

Purification of native CPE to near-homogeneity required isolation of chloroplasts. Additionally, recombinant pre-LHCP, complete with its transit peptide, was generated. The high affinity CPE has for the transit peptide of the precursor was used to affinity purify CPE at low temperature to prevent CPE from cleaving the transit peptide from pre-LHCP. A protein was isolated that co-purified with the proteolytic activity. Rabbits were injected with 100 μg of the purified protein (the 145/143 kDa doublet) that eluted from continuous-flow gels (SDS-PAGE). The antiserum against the doublet was pre-cleared of all nonspecific IgGs by isolating all other chloroplast soluble proteins (combining fractions that did not contain the 145/143 kDa proteins and attaching them to an insoluble matrix) and incubating them with the antiserum. Only after centrifugation was the antiserum employed to investigate the specificity of the cleavage reaction, i.e. to establish that the antiserum would immunodeplete the processing activity. The precleared antiserum was then used to screen a pea expression library for a cDNA coding for CPE. The identity of the cDNA was further verified using IgGs affinity purified using the 145/143 kDa doublet bound to nitrocellulose. The cDNA was sequenced (SEQ ID NO:1), and a reading frame was established. CPE is a very large protein, consequently not amenable to sequencing or identification of a full length cDNA. Another problem is that transcripts are of low abundance. The original cDNA coded only for the carboxy half of CPE.

Nevertheless, to unequivocally establish that the original cDNA coded for CPE, an expression construct was made, and the 65 kDa peptide was synthesized in E. coli. Antibodies were then made against the peptide, which were used in immunoblotting experiments. These antibodies recognized only the 145 and 143 kDa proteins in a chloroplast soluble extract, confirming the identity of the cDNA. The antibodies against the 65 kDa peptide, however, recognize only the denatured protein (as on Western blots) and thus could not be used to continue screening the library. The primary antiserum is extremely rare and hard to obtain, therefore it was not used for further screening. Therefore, subfragments of the cDNA were used to continue screening a library for the 5' end of the gene, and to design oligonucleotides for PCR. Additional methods and results relating to isolation of the cDNAs are presented below.

A 2.1 kb Xho I fragment containing an open reading frame (ORF) of 542 amino acids, equivalent to ~65 kDa, was subcloned and the ORF was overexpressed as a GST fusion protein in E. coli. The GST-fusion protein was recovered in soluble extracts, and purified by affinity chromatography. In immunoblot experiments, antibodies against the GST-fusion protein (anti-GST-fusion serum) recognized a protein of ~95 kDa from transformed E. coli lysates, as predicted from the size of GST and the insert ORF (FIG. 1). The anti-GST fusion serum also recognized the 145 and 143 kDa proteins in a chloroplast soluble extract in a one-to-one ratio. No other chloroplast proteins were detected. In the reciprocal experiment, the anti-145/143kDa serum recognized only the GST-fusion protein in the E. coli extract, as well as the 145/143 kDa doublet in the chloroplast extract used as a control. These results establish that the cDNA codes for the carboxy terminus of either the 145 or 143 kDa protein, and confirm that the correct ORF was expressed in E. coli. It was not possible to assign the cDNA to either the 145 or 143 kDa proteins because the anti-GST-fusion serum had an equal affinity for both proteins. It seemed likely that the 145/143 kDa proteins were either isoforms encoded by two related genes or represented posttranslational modification of a single gene product. Alternatively, the presence of the protein doublet could be an electrophoretic artifact, and there may be only one protein present. cDNA results suggest a single protein of about 140 kDa molecular weight.

To obtain the 5' end of the gene, a randomly primed cDNA library was screened using labeled restriction enzyme fragments. Two additional clones were identified. One contained a 1.7 kb insert that overlapped with the 5' end of the 2.7 kb fragment by 131 bases. The other cDNA (0.96 kb) overlapped by 0.57 and 0.52 kb with the 2.7 kb and 1.7 kb fragments, respectively. The three cDNAs showed complete sequence identity in their overlapping regions, indicating that they originated from the same gene. To assess whether the full sequence of the transcript was encoded by these cDNAs, 5' RACE PCR was carried out using poly(A)$^+$ RNA and two nested oligonucleotides near the 5' end of the 0.96 kb clone (see FIG. 2 (SEQ ID NO:1) for their position). The major PCR product of ~1.5 kb extended beyond the 5' end of the 1.7 kb fragment by only 62 bases. The sequencing results indicated that the full-length cDNA is 4.3 kb, codes for a polypeptide of 1259 amino acids, or 140 kDa, (SEQ ID NO:13) and contains presumptive 5' and 3' untranslated regions of 116 and 417 bases, respectively (FIG. 2). The ORF was also confirmed by microsequence analysis of a tryptic peptide released from the 145/143 kDa doublet. (SEQ ID NO:13)

The poly (A)$^+$ tail at the 3' end of the cDNA (SEQ ID NO:1) indicates that the 140 kDa polypeptide (SEQ ID NO:13) is encoded by the nuclear genome. Examination of the primary sequence of the 140 kDa polypeptide (SEQ ID NO: 13) revealed that its N-terminal region has characteristics of a transit peptide (Gavel et al., 1990), i.e. it is rich in Ser and Thr (28 within the first 100 residues), and primarily basic. Asp and Glu residues make-up 12% of the remainder of the protein, which has a predicted pI of 5.8. The lack of a good consensus sequence, as well as the variable length of transit peptides of proteins targeted to the chloroplast, makes it difficult to identify a cleavage site. However, in vitro import experiments using a truncated form of the precursor, synthesized by in vitro transcription/translation, (obtained from Promega) have confirmed the functional role of the transit peptide-like region and indicate that it is about 7 kDa.

When plants are grown in the dark many nuclear-encoded proteins of the photosynthetic apparatus are not synthesized, in particular those involved in the light reactions such as LHCP Bennett et al., 1984). However, the plastid performs a number of other essential metabolic processes besides photosynthesis, e.g. fatty acid and amino acid synthesis, that are active in the dark (Kirk et al., 1978). To investigate whether expression of CPE is light-dependent, first the level of CPE poly(A)$^+$ mRNA was compared from plants grown in the dark to those grown in the light. The steady state amounts of CPE mRNA (~4.0 kb) relative to total poly(A)$^+$ mRNA were the same under both growth conditions (FIG. 4A). Using the anti-GST fusion serum, the amount of the 145/143 kDa doublet was examined by immunoblots. Plastids were isolated from plants greened for 0, 6 and 24 hours, or grown under the normal light:dark cycle (16:8 h), and equivalent amounts of soluble protein were analyzed. Examination of membrane and soluble protein by Coomassie-stained gels showed no LHCP at the 0 hr time point, and a low level of Rubisco; both increased dramatically by 24 hrs. Nearly the same amount of the 145/143 kDa doublet was detected in the dark and over the greening period (FIG. 4B, lanes 1–4). Because no decline in the level of CPE was observed during a time when there is a large increase in the amount of Rubisco accumulating in the stroma, these results indicate that the absolute amount of CPE increased proportionally. The same extracts prepared from dark and light-grown plants were tested for CPE activity using pre-LHCP as a substrate in an organelle-free processing assay (Abad et al., 1989). Pre-LHCP was cleaved to approximately the same level in each reaction (FIG. 4C, lanes 1–5), producing the expected 25 kDa mature form of LHCP (Lamppa et al., 1987). Taken together, these results show that CPE does not depend on light for expression in pea plants, but suggest that increased synthesis accompanies the import of nuclear-encoded proteins which begin to rapidly accumulate upon exposure to light.

To determine if CPE is synthesized and active in organelles not involved in photosynthesis, plastids were isolated from pea roots and soluble extracts prepared. The anti-GST fusion serum recognized both the 145 and 143 kD proteins, which were equally abundant, but overall levels were 5–10 fold lower than found in leaf extracts (FIG. 4B, lane 5). Significantly, preLHCP was cleaved in the organelle-free assay using the root extracts (FIG. 4C, lane 7) despite, the fact that root plastids do not normally see preLHCP as a substrate. These results suggest that CPE is necessary in roots for the import and maturation of proteins targeted to the plastid for non-photosynthetic functions.

These results demonstrate that CPE expression is not light-dependent in pea. Not only are mRNA and the 145/143 kDa proteins present in the dark, but cleavage of preLHCP occurs with etioplast extracts. Mature LHCP, on the other hand, was not detectable in the etioplast membranes, in agreement with the fact that there is essentially no expression of the LHCP genes in the dark (Bennett et al., 1984). Thus, the synthesis of CPE is regulated separately from LHCP, and can precede the light-dependent accumulation of products needed for photosynthesis. Furthermore, CPE is active in root plastids, which supports the conclusion that CPE is not preLHCP-specific, but rather has broader substrate specificity as a general stromal processing peptidase. Many metabolic pathways of the plastid, e.g. for fatty acid and amino acid biosynthesis, are functional in the dark and in other organs besides leaves (Kirk et al., 1978), and depend on the import of numerous proteins from the cytosol. Indeed, immunodepletion experiments indicate that cleavage of the precursor of ACP, a key protein involved in fatty acid synthesis, requires the 145/143 kDa proteins (Oblong et al., 1992). It is likely therefore that CPE expression is activated by an endogenous developmental program that begins at an early stage of plastid biogenesis. Nevertheless, it appears that light can stimulate the synthesis of CPE in parallel with the large influx of nuclear-encoded proteins which occurs during greening and assembly of the photosynthetically competent organelle.

An aspect of the invention is the cDNA encoding the primary structure of the 140 kDa polypeptide (SEQ ID NO:13), CPE. The CPE cDNA (SEQ ID NO:1) has ben recorded with GenBank and given the accession number U25111. As described herein, antibodies (rabbit anti-145/143 kDa serum) raised against the 145 and 143 kDa proteins, originally purified from pea chloroplasts (Oblong et al., 1992), were used to screen a λZap pea expression library made from poly(A)$^+$ RNA. A cDNA clone was isolated containing a 2.7 kb insert with a poly (A)$^+$ tail, indicating that it corresponded to the 3' end of the transcript.

Databases (Swiss Protein, EMBL, Genbank, DDBJ) were searched to determine if the 140 kDa polypeptide is related to any known proteases. Beginning at Leu-222, the 140 kDa polypeptide (SEQ ID NO:13) shows strong similarity to a new family of metalloendopeptidases, the pitrilysins (Rawlings et a., 1993). The pitrilysin family includes *E. coli* protease III (SEQ ID NO:4) (Finch et al., 1986), human (SEQ ID NO:5) (Affholter et al., 1988) and Drosophila (Kuo et al., 1990; Becker et al., 1992) insulin-degrading enzymes (IDE), which are ~110 kDa and have related substrate specificities in vitro. A zinc-binding His—X—X—Glu—His (HXXEH) motif (SEQ ID NO:2), which defines this family, is located at position 238–242 of the 140 kDa polypeptide (SEQ ID NO:13). It has now been recognized in a growing list of metalloendopeptidases including the MPP subunit β (Witte et al., 1988; Hawlitschek et al., 1988; Paces et al., 1993), an N-arginine dibasic convertase (Pierotti et al., 1994), a hypothetical protease YDDC (SEQ ID NO:6) within the glutamate decarboxylase operon of *E. coli* (Swiss protein no. P31828), and a *Bacillus subtilis* ORF near the diaminopimelate operon (Chen et al., 1993). A comparison of the 140 kDa polypeptide (SEQ ID NO:13) with representatives of this family (FIG. 3) reveals 25–30% sequence identity, or 35–40% similarity, in an N-terminal region of 130 amino acids which continues beyond the HXXEH-motif (SEQ ID NO:2) to residue 326; thereafter sequence similarity becomes more scattered. Overall, YDDC (SEQ ID NO:6) shows the most sequence-relatedness to the 140 kDa polypeptide (SEQ ID NO:13).

Figure 4:
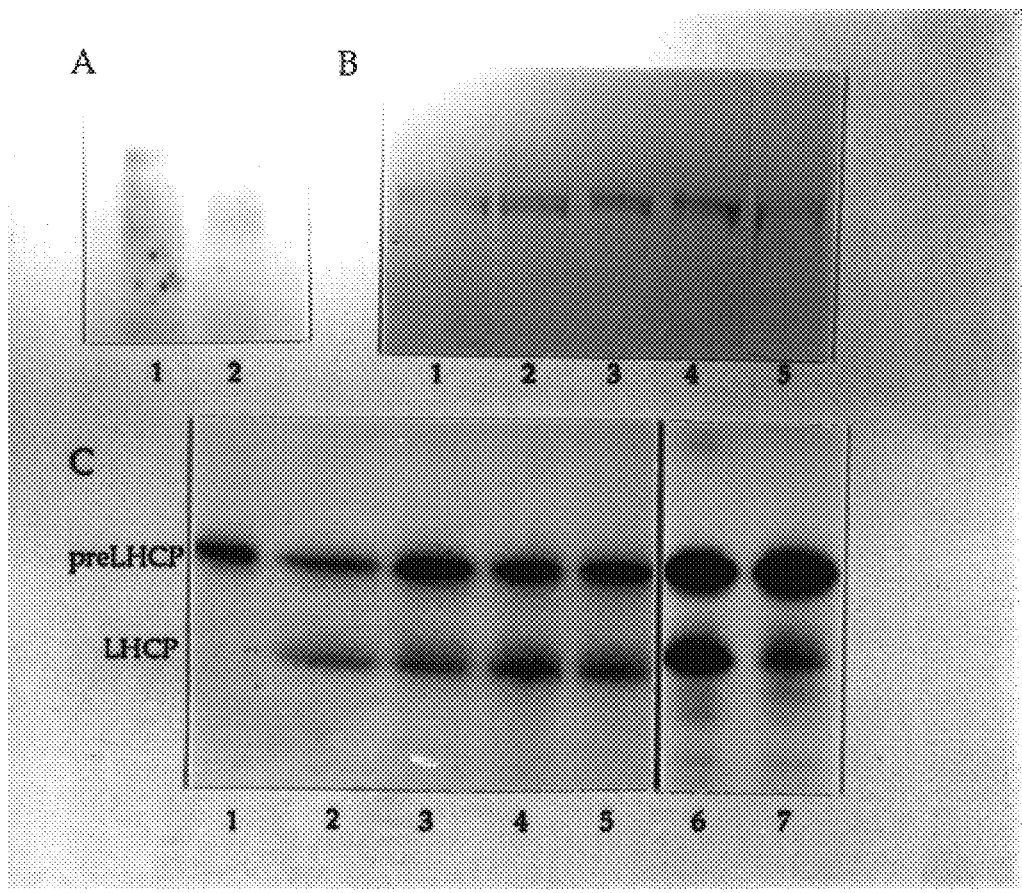

Conservation extends beyond the HXXEH motif (SEQ ID NO:2), which is required for catalysis (Becker et al., 1992; Perlman et al., 1993; Gehm et al., 1993), suggesting similar evolutionary origins of the chloroplast processing enzyme and these other metalloendopeptidases. Significantly, however, their substrate specificities have diverged. As shown in FIG. 6, an Arabidopsis genomic clone has been partially sequenced (SEQ ID NO:10). The sequence of ~1.5 kb of the promoter is known, which likely contains the regulatory elements responsible for CPE gene expression. CPE itself contains a transit peptide, and its removal may be via an autocatalytic mechanism. Transit peptides are likely to be divergent across species, while the primary structure of mature CPE is likely highly conserved. Thus, aligning the sequences of CPE from Arabidopsis (SEQ ID NO:10) and pea (SEQ ID NO:9) ; in FIG. 6 shows that there is considerable sequence divergence between the two open reading frames that dramatically switches to nearly 95 % similarity further indicating that this position marks the beginning of the mature, functional protein involved in catalysis. Moreover, there is perfect alignment of the zinc binding domain, HXXEH, that is likely required for catalysis and peptide bond cleavage. CPE shares 25–30 % identity, concentrated near the N-terminus of the 140 kDa polypeptide (SEQ ID NO:13), with protease III (SEQ ID NO:4), IDE, and MPP. Expression of CPE in leaves is not light-dependent (FIG. 4). Indeed, transcripts are present in dark-grown plants, and the 145/143 kDa doublet (SEQ ID NO:13) and proteolytic activity are both found in etioplasts, as well as in root plastids. Thus, CPE appears to be a necessary component of the import machinery in photosynthetic and non-photosynthetic tissues, and functions as a general processing peptidase in plastids.

From the diversity of substrates cleaved by members of this metalloendopeptidase family one would predict that the determinants for substrate recognition reside in novel regions of each enzyme, outside of the HXXEH-containing domain. (FIG. 5). It is relevant that mutations in the HXXEH sequence (SEQ ID NO:2) block proteolysis but not binding of IDE to insulin (Gehm et al., 1993). Structural features are likely to exist in each substrate to facilitate specific cleavage. For processing by CPE, as well as MPP, the precursor N-terminal targeting signal and cleavage site per se are undoubtedly important (Clark et al., 1991; Yang et al., 1991), but it is currently unclear how they participate in the reaction. The cloning of CPE permits exploration of its interactions with precursors targeted to the plastid, and by mutational analyses, to investigate mechanism of precursor cleavage.

To use the cDNA encoding a plastid processing enzyme in recombinant technology, the cDNA is linked to an inducible promoter and transformed into E. coli as an expression cassette. Upon induction, the processing enzyme is synthesized as a recombinant enzyme and recovered as either a soluble or insoluble protein. For example, the carboxy half (~65 kDa) of the polypeptide (SEQ ID NO:13) of FIG. 2 is synthesized in E. coli, and recovered as a soluble protein when cells are grown at 27° C. Similar strategies are available to recover the full-length enzyme in an active form. Because the enzyme likely cleaves many different kinds of polypeptides used in numerous biosynthetic pathways, e.g. fatty acid synthesis, amino acid synthesis, terpene synthesis, starch accumulation, and nitrogen and sulfur reduction that are found in the plastid, mature forms of these proteins are generated by cleavage in vitro with the recombinant enzyme. The N-terminus of the cleaved protein can be sequenced in order to establish the processing site. After the sequence of the processing site is known, cDNAs are constructed such that mature proteins can be synthesized either in vitro or in large quantities as recombinant proteins. Alternatively, mature proteins can be recovered directly from cDNAs encoding pre-proteins that are subsequently processed in an organelle-free processing assay (Lamppa et al., 1987).

Novel proteases with targeting specificity may be constructed using subdomains of the plastid processing enzymes or structurally altered forms of the enzymes generated through site-directed mutagenesis. The ability of the enzyme to recognize a substrate is examined by both binding assays in vitro and an organelle-free processing assay (Lamppa et al., 1987). Results indicate that the enzyme recognizes the transit peptide of pre-proteins, and each transit peptide contains features that direct cleavage at the correct site, that is, between specific amino acids. Because cleavage sites vary, the transit peptide-mature protein region of each pre-protein may contain sufficient information for recognition by the processing enzyme. Subtle changes in the enzyme may affect the efficacy of cleavage through changes in substrate recognition and affinity.

To understand and manipulate the mechanism underlying precursor recognition and selective processing, genes coding for the 145 and 143 kDa proteins are useful to describe the primary structure of the proteins. cDNAs have been isolated, initially employing antibodies to the 145/143 kDa doublet (SEQ ID NO:13), that code for a 140 kDa polypeptide (SEQ ID NO:13) with a transit peptide. Antibodies raised against a recombinant protein corresponding to the C-terminus of this polypeptide recognize only the 145/143 kDa doublet (SEQ ID NO:13) in a chloroplast extract. The 145/143 kDa proteins are expressed both in light and dark-grown shoots, and are also present in root plastids. The presence of CPE in root plastids is significant, providing evidence that the enzyme has broad substrate specificity and is utilized for precursor maturation where the organelle carries out non-photosynthetic processes.

The ability of CPE to cleave a large diversity of pre-proteins with differing primary sequences suggests that CPE recognizes secondary structural features which determine selective peptide bond hydrolysis. Since these features vary between substrates, CPE may have a different affinity for different precursors. Site-directed mutagenesis of CPE, outside of the $Zn^{+2}$ binding motif (SEQ ID NO:2), is used to yield an enzyme with an altered substrate specificity. Specificity may either become more selective, or relaxed, allowing for cleavage of a broader range of substrates. Careful manipulation establishes the exact nature of determinants for cleavage that reside in CPE itself, as well as the precursor substrate, making them transferrable to other polypeptides.

As will be seen in the examples herein, overexpression of CPE or antisense cDNA of CPE in transgenic plants produces herbicidal function.

EXAMPLES

EXAMPLE 1

Use of Antisense and Sense CPE Constructs As Herbicides

Antisense transformants. The 5' region of the CPE gene, equal to 2.2 kb of non-translated leader sequence and coding region was inserted in reverse orientation downstream of the Cauliflower Mosaic Virus (CaMV) 35S promoter using recombinant DNA methods. Cloning cDNA into an expression vector directs synthesis of antisense DNA, which is complementary to endogenous mRNA and will effectively prevent protein translation or target RNA for degradation. The antisense construct was transformed into tobacco using the natural vector, *Agrobacterium tumefaciens*. The antisense construct also contained the neomycin phospotransferase gene to allow transformants to be selected by their resistance to the antibiotic kanamycin. Plants were regenerated in tissue culture, and transferred to soil pots for full growth and seed production. Seeds were harvested and planted on sterile media with antibiotics to select for kanamycin resistance. Plants were grown in a light:dark cycle of 16 h:8 h.

Sense transformants. The full-length gene equal to 4 kb was inserted downstream of the CaMV 35S promoter, and transferred into tobacco as described above.

Transgenic tobacco seeds, carrying either the antisense or sense CPE constructs, were imbibed on sterile media, and their phenotypes monitored during growth. The antisense transgenic plants showed normal germination, but growth was slower than wild type plants. In addition, the first true leaves were chlorotic. Analysis of chloroplasts by electron microscopy showed that they were fewer in number and filled with starch grains. Hence, it appears that altering the levels of CPE has a major impact on organelle biogenesis. Seeds from one transgenic plant with the sense construct, with the goal of causing co-suppression, have thus far been analyzed. They are either embryo lethal (do not germinate) or germinate and show very slow growth. Leaves are narrow, and mottled. Analysis of chloroplasts showed that they are smaller than normal (about one third the size).

EXAMPLE 2

Overexpression and Isolation of Recombinant CPE

The cDNA for CPE is recombinantly synthesized as a fusion protein, wherein CPE is fused to a tag/linker molecule. A CPE fusion protein vector is generated. CPE cDNA (SEQ ID NO:1) is introduced downstream from an appropriate linker molecule such as glutathione S-transferase (GST) such that upon expression of the resulting vector, the CPE is expressed as a fusion protein. After the CPE fusion vector is generated, it may be introduced into a suitable host, such as *E. coli,* yeast, or insect cells. The expressed fusion protein is isolated from the host lysate via affinity chromatography. In GST systems, glutathione is attached to the column matrix. As the lysate containing the fusion protein passes over the column, the glutathione binds the fusion protein. After washing the column, the fusion proteins are eluted under the appropriate conditions, usually high concentrations of glutathione. Upon isolation of the fusion protein from the host, the tag molecule can be selectively, enzymatically removed yielding pure CPE which can then be used for other experiments, or commercially exploited.

In another example, proteins of interest are synthesized directly in *E. coli,* recovered, and cleaved to their mature forms in test tubes containing CPE. This example obviates the need of identifying where the mature protein begins.

Alternatively, CPE cDNA (SEQ ID NO:1) can be recombinantly inserted into an appropriate expression vector, such as a T7 expression system *E. coli* and isolated without the need for synthesizing a fusion protein. Alternatively expression systems for yeast, or insect cells could be employed. The expression vector can be transformed into the appropriate host, such as *E. coli,* yeast, or insect cells, and lysates containing CPE protein isolated. The antiserum that recognizes CPE protein is attached to the matrix of an affinity column. CPE-containing lysate is passed over the affinity column, and CPE is isolated without the additional requirement of removing a reporter molecule from a fusion protein. The histidine rich nature of CPE may allow purification using a nickel-matrix.

cDNA indicates the nucleotide sequence (SEQ ID NO:1) of FIG. 2 or a substantially similar sequence, wherein "substantially similar" is defined as a sequence in which (1) nucleotides are substituted that do not affect the protein encoded by the amino acid sequence of FIG. 2 (SEQ ID NO:13), (2) the nucleotides encode an amino acid sequence that is the equivalent of that shown in FIG. 2 (SEQ ID NO:13), wherein "equivalent" means that the structure and function of the three dimensional protein formed by the amino acid sequence is that of the enzyme claimed herein. Also "substantially similar" is defined as containing the catalytic domain and regions conferring substrate specificity.

EXAMPLE 3

Plant Lines Overexpressing CPE and Commercially Desirable Molecules

Transgenic plants overexpressing CPE, generated as in Example 1 (transgenic tobacco), are used to overexpress and harvest commercially desirable proteins directly or those necessary to produce other types of molecules. In one example, the biosynthetic enzymes required to make terpenoids, which are molecules responsible for fragrance in perfume, are synthesized as fusion proteins with the transit peptides responsible for plastid targeting. cDNA for the transit peptide/enzyme is recombinantly placed in a vector that naturally transforms plants, such as *Agrobacterium tumefaciens.* When the vector is introduced into the appropriate host plant, it will direct overexpression of the enzyme, which is targeted to a plastid. Under this scheme, the enzymes are targeted to the plastids, and once there, will have the transit peptide enzymatically removed by CPE. The plastids are purified from the rest of the plant lysate, and the enzyme, in its active state, is isolated from the plastid.

Alternatively, the transit peptide/protein vector is introduced into non-transgenic plants expressing normal levels of CPE. Potentially, more protein may be expressed than can be processed by the endogenous CPE levels, while not interfering with the transport of protein to the plastid. Under this scenario, protein is isolated via affinity chromatography using CPE and its high affinity for the transit peptide as the ligand. Under suitable conditions, that is preventing enzymatic activity of CPE, such as low temperature, the transit peptide fusion protein is isolated and eluted. Furthermore, after the transit peptide/protein is purified, the transit peptide can be enzymatically removed through action of CPE under appropriate reaction conditions.

EXAMPLE 4

Selective Inactivation of CPE from Selected Plant Species

Sequence alignment of CPE cDNA from pea (SEQ ID NO:9) and Arabidopsis (SEQ ID NO:10) suggests that the open reading frame for mature CPE is conserved among species while the transit peptide encoding region and the 5' and 3' flanking regions are divergent. (See FIG. 3 for an example of sequence alignment). Moreover, neither animal nor bacterial metalloendopeptidase genes demonstrate the same flanking sequences as the plant CPE, nor do they encode transit peptides, thereby ensuring that plant CPE antisense molecules would not affect animal cell growth. Because there is considerable flanking sequence divergence, selective inactivation of endogenous CPE is possible. Transgenic tobacco plants expressing CPE antisense molecules demonstrated retarded growth and altered organelle biogenesis, presumably due to the antisense selectively binding CPE RNA, thereby lowering the effective endogenous levels of CPE. Retarded growth is a desirable herbicidal phenotype. Thus, in an example, an antisense CPE construct is engineered that is specific for Arabidopsis CPE. The Arabidopsis antisense CPE construct is cloned into a naturally occurring microorganism capable of entering plants in a non-deleterious fashion, such as a plant virus, or *Agrobacterium tumefaciens.* The microorganism is applied in a suitable fashion to fields of pea plants. The microorganism carrying the Arabidopsis CPE antisense construct will infect all plants present, but the CPE specific to Arabidopsis will selectively inactivate the CPE in the weed plants, thus serving as an effective herbicide without exhibiting any toxic side effects for animals or other crop consumers. Alternatively, the CPE antisense construct can be introduced into plant subpopulations through traditional genetic crosses.

MATERIALS AND METHODS cDNA Isolation and Sequencing

A λZapII (Stratagene) cDNA library, constructed using mRNA from dark-grown pea seedlings greened for 24 hours, was screened by methods of Sambrook et al., (1989) with polyclonal antiserum raised against the 145/143 kD doublet (Oblong et al., 1992). Digoxigenin-labeled DNA restriction enzyme fragments from the λZap clone were made using the Genius Kit (Boehringer Mannheim Biochemicals) and were used to screen a λgt11 library (Clonetech) made by random priming and priming on the poly(A)+ tail of mRNA from 7 day old dark-grown pea seedlings. Isolation of the 5' end of the cDNA was accomplished using 5' RACE (Rapid Amplification of cDNA Ends) PCR essentially as described by the vendor (GibcoBRL) using 10 ug of poly(A)+ RNA from etiolated plants and the oligonucleotides described Clones were serially deleted with exonuclease III and sequenced with the Sequenase Version 2.0 kit (U. S. Biochemicals).

Isolation of Arabidopsis Genomic Clones Coding for CPE

Using the pea gene as a probe, an Arabidopsis genomic library was screened for genes homologous to pea CPE. Three genomic clones were identified with inserts of approximately 12 kb. One of these, called 9A was partially sequenced by the didoxy claim termination method. Two other clones (2A and 12A) were also identified.

The 9A Arabidopsis clone has been partially sequenced. The sequence of ~1.5 kb of promoter is known that should contain regulatory elements for CPE gene expression, and nearly kb of exon and intron sequence has been determined. This information has helped to establish the likely start of mature CPE based on the fact that transit peptides are not highly conserved, but mature CPE is expected to be highly conserved. That is, the Arabidopsis (SEQ ID NO:10) and pea (SEQ ID NO:9) amino acid sequences have been aligned (FIG. 6), and there is considerable sequence divergence of the two open reading frames that dramatically switches to almost 95 % similarity, where an indication that this marks the beginning of the functional, mature protein involved in catalysis. In addition, perfect alignment of the domain containing the zinc-binding motif exists, HMIEH, that is likely to be required for catalysis and peptide bond cleavage.

Preparation of GST-fusion Protein and Antiserum

A 2.1 kb Xho I fragment was ligated into the Xho I site of pGEX-KG to create an in-frame fusion of glutathione-S-transferase (GST) and the C-terminus of CPE. The GST-fusion protein was expressed in E. coli strain BL21 at 25° C., affinity purified using glutathione-agarose (Sigma) and eluted with 10 mM glutathione (Guan et al., 1991). Rabbit polyclonal antiserum was generated using ~1 mg of GST-fusion protein.

RNA Isolation and Northern Blotting

Total RNA was isolated from leaf tissue of 7 day old light-grown or 10-day old dark-grown pea plants as previously described (Lamppa et al., 1985). Poly(A)+ RNA was isolated using Poly(U)-Sephadex (Gibco BRL) as suggested by the manufacturer. Poly(A)+ RNA (10 ug) was separated on a glyoxal/DMSO gel and blotted to a nylon membrane (Boehringer Mannheim Biochemicals) as described (Lamppa et al., 1985), then UV cross-linked (Hoeffer UVC 1000). Hybridization at 65° C. for 18 h with digoxigenin-labeled DNA probe (20 ng labeled probe/ml) and chemiluminescent detection were carried out as recommended (Borchert et al., 1989).

Plastid Isolation

Chloroplasts and etioplasts were isolated (Abad et al., 1991) from pea (Pisum sativum, Laxton's Progress #9). For the greening experiment (FIG. 4B, C) plants were grown for 9 days in the dark then exposed to light before harvesting. Root plastids were prepared (Borchert et al., 1989) from plants grown in Turface Regular (Applied Industrial Materials Co.) for 8 days.

Protein Analysis

Radiolabeled precursor synthesis, in vitro organelle-free processing reactions, SDS-PAGE analysis and immunoblot detection of CPE were carried out as described (Abad et al., 1989; Oblong et al., 1992). For protein sequencing the 145/143 kD proteins were isolated by preparative SDS-PAGE (Oblong et al., 1992), and tryptic peptides were sequenced by Edman degradation at Rockefeller University.

Antisense and Sense Constructs, and Plant Transformation

A full-length cDNA was constructed by combining two partial cDNA clones first in the vector p1B130. The antisense construct was made by digesting the full-length CPE cDNA with EcoRI which produced a 2.2 kb fragment encoding the transit peptide and half of the mature protein. This was then moved into the plasmid pBICaMV, containing the CaMV 35S promoter, in reverse orientation which was transformed into Agrobacterium tumefaciens. Leaf discs from tobacco plants were transformed with Agrobacterium carrying the antisense CPE fragment by inoculation and selection for kanamycin resistance. Calli were grown on sterile media, and upon the regeneration of kanamycin resistant shoots, these were excised and transferred to sterile media with an auxin to cytokinin ratio that promoted root formation. After roots had formed, the plants were transferred to soil, and plants were grown to maturity, self-fertilized, and seeds harvested. The phenotypes of plants grown from this seed population were analyzed.

The transformants carrying the sense constructs were prepared similarly, only the full-length cDNA, bounded by restriction enzyme sites Sma I and Msc I yielding a 4.4 kb fragment, was cloned into pBICaMV.

DOCUMENTS CITED

Abad, M. S., Oblong, J. E. & Lamppa, G. K. (1991) *Plant Physiol.* 96, 1220–1227.

Abad, M. S., Clark, S. E. & Lamppa, G. K. (1989) *Plant Physiol.* 90, 117–124.

Affholter, J. A., Fried, V. A. & Roth, R. A. (1988) *Science* 242, 1415–1418.

Bassham, D. C. Bartling, D., Mould, R. M., Dunbar, B., Weisbeek, P., Herrmann, R. G. & Robinson, C. (1991) *J. Biol. Chem.* 266, 23606–23610.

Becker, A. B. & Roth, R. A. (1992) *Proc. Natl. Acad. Sci. USA* 89, 3835–3839.

Bennett, J., Jenkins, G. I. & Hartley, M. R. (1984) *J. Cell. Biochem.* 25, 1–13.

Borchert, S., Grobe, H. & Heldt, H. W. (1989) *FEBS Letters* 253, 183–186.

Chen, N.-Y., Jiang, S.-Q., Klein, D. A. & Paulus, H. (1993) *J. Biol. Chem.* 268, 9448–9465.

Clark, S. E. & Lamppa, G. K. (1991) *J. Cell. Biol.* 114, 681–688.

Engler-Blum, G., Meier, M., Frank, J. & Müller, G. A. (1993) *Anal. Biochem.* 210, 235–244.

Finch, P. W., Wilson, 05–218.

Robinson, C. & Ellis, R. J. (1984) *Eur. J. Biochem.* 142, 337–342.

Sambrook, J., Fritsch, E. F. & Maniatis, T., *Molecular Cloning: A Laboratory Manual* (Cold Spring Harbor Laboratory Press, Cold Spring Harbor, 1989), pp. 12.16–12.20.

Schnell, D. J., Kessler, F. & Blobel, G. (1994) *Science* 266, 1007–1012.

VanderVere, P., Bennett, T., Oblong, J. and Lamppa, G. (1995) *Proc. Natl. Acad. Sci. USA* 92, 7177–7181.

Witte, C., Jensen, R. E., Yaffe, M. P. & Schatz, G. (1988) *EMBO J.* 7, 1439–1447.

Yang, M., Géli, V., Oppliger, W., Suda, K., James, P. & Schatz, G. (1991) *J. Biol. Chem.* 266, 6416–6423.

---

I claim:

1. A cDNA having a nucleotide sequence as in SEQ ID NO:1 and encoding for a plastid processing enzyme from a plant and wherein said enzyme is a member of a family of metalloendopeptidases, said family designated the pitrilysins, said enzyme capable of cleaving a transit peptide from the N-terminus of a preprotein that is targeted to a chloroplast, said cleaving resulting in a biologically active protein and a transit peptide, and wherein said enzyme has a zinc binding motif.

2. A cDNA having a nucleotide sequence as in SEQ ID NO:1 and containing 5' and 3' untranslated regions of 116 and 417 bases, respectively, and encoding an endopeptidase (SEQ ID NO:13) having 1259 amino acids, said endopeptidase having an estimated molecular weight of 140 kDa and a zinc binding motif at positions 238–242 of SEQ ID NO:13.

3. A recombinant genetic method for producing a plastid processing enzyme, sad method comprising introducing into a suitable host cell an expression vector comprising a cDNA encoding the enzyme, wherein said cDNA has a nucleotide sequence as in SEQ ID NO:1, and placing the host cell in conditions that allow expression of the vector.

4. An antisense molecule directed to the cDNA of claim 1, wherein the antisense molecule consisting of the complementary sequence to residues 1–2,200 of SEQ ID NO: 1.

5. A cDNA having a nucleotide sequence as in SEQ ID NO: 1 and encoding for plastid processing endopeptidase from a plant, said endopeptidase having:

(a) an estimated molecular weight measured by SDS polyacrylamide gel electrophoresis of about 140 kDa;

(b) a zinc binding motif; and (c) a protease activity of cleaving a transit peptide from the N-terminus of a preprotein that is targeted to a chloroplast, said cleaving resulting in a biologically active protein and a transit peptide.

6. A cDNA having a nucleotide sequence as in SEQ ID NO:1.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 4337 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:1:

```
GGATCCATTT CTGAGAAGTA GAAAGAAAAA AAAAATCTGA AGAAAAATC AAGAGGTTGA        60

GTGCGTTGGT GTGCTTGCGT TTCTGTTAAG GTTAAGCTGC TACGCATACG GTGGTTATGC      120

CAATGGCTGC TTCAACTTCA ACCTCATCTC TCTCCGTCGT TGGAACTAAC CTCTCTCTCC      180

CTCCGCATCG TCATCATCGC CACTTTCACT CTCCCTCTTC AATCTCCACT CGTATCCGTA      240

CCAACCGTCT CTTCTTATCC TCTTCTCTCG CGTTCTCTTC TCCACGTGAT GCAAGAGTTG      300

TTCACGCTGG ATTAGGTTTA CGGAGGAATA CGCCGGATGT TTGGAAACAC TATTCCTCCG      360

TCCTTTCTCA ACCGACTGCA CCGGTACCGG TACGGCAAAG CTGTACTTCA TGCTGTCTTG      420

CTTCCGCAAA GAAACGCCGT TCAAATCTCC CGAGATTTGT TCCTGGAGCT TTTTTTGATA      480

GTTCTTCTTT TGGATTATCT AAGGATAAGC TTCGTCACGC TTCTGTTAAG CGGGTTCAGC      540

TTCCGCATGC AACTGTTGGT CCAGATGAGC CACATGCCGC TAGCACAACT TGGCAGGAGG      600

GCGTTGCTGA AAAACAAGAC TTAAGTTTGT TTGATTCTGA ACTGGAAAGG CTAGAGGGTT      660

TTTTGGGTTC TGAACTTCCA TCTCACCCTA AGTTGCATCG GGGTCAGCTA AAGAATGGGA      720

TTCGTTATTT GATTCTGCCA AATAAAGTTC CTCCAACAAG GTTTGAAGCA CACATGGAAG      780

TTCATGTAGG ATCAATAGAT GAAGAGGATG ATGAACAAGG AATTGCACAT ATGATTGAAC      840

ATGTTGCTTT CTTAGGAAGT AAAAAACGCG AGAAGCTTTT GGGAACAGGA GCCCGTTCAA      900

ATGCTTATAC AGATTTTCAC CATACAGTGT TTCACATCCA TTCTCCTACC TCTACCAAGG      960

ATTCTGATGA TCTTCTTCCA TCTGTTCTGG ATGCCCTGAA TGAGATAACC TTCCACCCAA     1020

ATTTTCTTGC ATCAAGAATA GAAAAAGAAC GGCGTGCTAT ACTCTCAGAG CTTCAAATGA     1080

TGAACACAAT AGAGTATCGG GTTGATTGCC AGTTGTTACA ACATTTGCAT TCTGAAAACA     1140

AGCTGAGCAA AAGGTTTCCA ATTGGATTAG AAGAACAGAT AAAGAAGTGG GATGCAGATA     1200

AAATAAGAAA ATTTCATGAG CGCTGGTATT TCCCTGCAAA TGCAACATTG TACATTGTAG     1260

GGGATATTGG TAACATTCCA AAAACTGTTA ACCAGATTGA AGCTGTTTTT GGACAAACTG     1320

GTGTAGACAA TGAGAAAGGT TCTGTAGCCA CTTCAAGTGC ATTTGGTGCA ATGGCTAGTT     1380

TTCTAGTTCC TAAGCTCTCT GTTGGTCTTG GTGGAAATTC TATTGAAAGA CCAACCAATA     1440

CAACGGATCA ATCAAAAGTA TTTAAAAAGG AGAGACATGC TGTTCGTCCT CCTGTGAAGC     1500

ATACTTGGTC ACTTCCTGGA AGCAGTGCAA ATTTGAAGCC ACCACAAATA TTTCAACACG     1560

AGTTGCTTCA AAACTTTTCA ATTAATATGT TCTGCAAGAT TCCAGTGAAT AAGGTTCAAA     1620
```

```
CATACCGAGA TTTGCGTATT GTCTTGATGA AAAGAATATT TTTGTCAGCT CTTCATTTTC      1680

GTATTAATAC GAGATATAAG AGTTCGAATC CACCATTCAC TTCAGTTGAA TTGGATCATA      1740

GTGATTCTGG AAGGGAAGGA TGTACTGTGA CCACTCTTAC CATAACTGCA GAACCAAAGA      1800

ATTGGCAGAA TGCTATTAGA GTTGCTGTTC ATGAGGTTCG CAGACTTAAA GAGTTTGGTG      1860

TTACTCAGGG TGAATTAACT CGCTATCTAG ACGCCCTTTT GAGAGATAGC GAACACCTAG      1920

CAGCCATGAT TGATAATGTA TCTTCTGTTG ACAACTTGGA TTTTATCATG GAAAGTGATG      1980

CTCTAGGCCA TAAAGTTATG GACCAGAGTC AAGGGCATGA AAGTTTAATT GCTGTTGCTG      2040

GGACAGTTAC CCTTGACGAG GTTAATTCTG TTGGTGCTCA GGTGTTAGAA TTTATAGCTG      2100

ATTTTGGAAA GCTTTCTGCA CCCCTTCCTG CAGCAATTGT TGCTTGTGTT CCGAAAAAAG      2160

TTCACATCGA AGGAGCTGGT GAAACAGAAT TCAAGATATC ATCAACTGAA ATAACAGATG      2220

CTATGAAAGC TGGATTGGAT GAGCCTATAG AGCCAGAACC CGAGCTCGAG GTTCCAAAAG      2280

AACTTGTACA GTCATCAACG CTACAAGAGT TAAAAAATCA GCGCAAGCCA GCCTTTATTC      2340

CAGTCAGTCC TGAAATAGAG GCTAAGAAGC TTCATGATGA GGAAACTGGA ATCACCCGCC      2400

TCCGCCTTGC AAATGGAATT CCCGTCAACT ATAAGATATC TAAAAGTGAA ACACAAAGCG      2460

GCGTGATGCG GCTGATTGTT GGTGGCGGAC GAGCAGCTGA GGGTTCTGAT TCAAGAGGAT      2520

CTGTGATTGT GGGTGTTAGG ACGCTTAGTG AGGGAGGTCG TGTTGGCAAC TTCTCAAGGG      2580

AGCAGGTTGA ACTTTCTGC GTAAATAACC AGATAAATTG CTCCTTAGAA TCTACGGAGG       2640

AGTTCATATC TTTGGAGTTT CGTTTTACTT TAAGGAATAA TGGGATGCGT GCAGCCTTTC      2700

AATTGCTTCA CATGGTGCTT GAGCATAGTG TCTGGTCAGA TGATGCTTTG GATAGAGCGA      2760

GGCAAGTGTA TCTGTCATAT TACCGATCAA TCCCCAAGAG CTTGGAACGC TCGACTGCTC      2820

ACAAACTTAT GGTTGCAATG TTGGATGGAG ATGAGCGATT TACTGAGCCT ACACCAAGTT      2880

CACTAGAAAA TCTAACTCTG CAATCTGTTA AGGATGCTGT AATGAATCAG TTTGTTGGAA      2940

ATAACATGGA GGTCTCCATT GTAGGTGATT TCACTGAGGA AGAGATTGAA TCATGTATTT      3000

TAGATTACCT TGGCACAGCT CAGGCCACGG GAAACTTTAA AAACCAGCAA CAAATTATCC      3060

CACCAACATT TCGATTATCT CCATCCAGTT TGCAGTCTCA AGAAGTTTTC TTGAATGACA      3120

CTGATGAGAG GGCATGCGCT TATATTGCTG GGCCTGCACC AAACCGTTGG GGTTTTACTG      3180

CAGATGGAAA CGACCTGTTA GAGACAATTG ATAATGCATC ATCAGTCAAT AATAATGGGA      3240

CAAAATCTGA TGCTCTACAA ACAGAAGGTG CTCCACGAAG GAGCCTCCGT AGTCATCCTC      3300

TTTTCTTTGG TATAACAATG GGACTGCTTT CTGAAATTAT AAATTCTAGG CTCTTCACAA      3360

CAGTCAGAGA TTCACTGGGC TTGACATACG ACGTGTCATT TGAATTGAAC TTGTTTGATA      3420

GGCTTAAACT AGGGTGGTAT GTGGTCTCTG TAACATCAAC TCCAAGCAAG GTGCACAAAG      3480

CTGTTGATGC ATGCAAGAAT GTTCTAAGAG GTTTGCATAG CAACGGAATT ACAGTCAGGG      3540

AATTGGACAG GGCTAAACGG ACCCTTCTTA TGAGACATGA AGCTGAAATT AAGTCAAATG      3600

CGTACTGGTT GGGATTGTTA GCTCACTTAC AATCGTCTTC TGTTCCAAGG AAGGACCTAT      3660

CATGTATCAA GGATTTAACG TCTCTATATG AAGCTGCTAC TATTGAGGAT ACATGCCTTG      3720

CATATGAACA GTTGAAAGTG GATGAAGATT CTCTATATTC ATGCATTGGG GTTTCTGGTG      3780

CTCAGGCTGC ACAAGATATA GCAGCTCCTG TAGAAGAGGA AGAAGCAGGT GAGGGTTATC      3840

CAGGGGTTCT TCCTATGGGA CGAGGTTTAT CTACAATGAC ACGGCCTACT ACCTAATTTT      3900

TTTGGATGAC AGGGTTGGTC TGCCCTGATT TAAGAGGAAG CCATGTCTGG AAGTTTAGTT      3960
```

```
ATACAGGTCT TGGTTCAAAG AATTGGCAGT ATATGTATTA CAAGAGACTG CTGGATTCAT    4020

TTAAAACATT CGAACCAGTC AGCATCCAAG CTGTTGGATC AATCCTAAGA AGTGGTTCTT    4080

GGCTTGCTAT TTATTTCCTT AATGTCCATT TATGTTTAGT TGAACCACTA ATAAACTATT    4140

ATCGCTGCTT ATACTTTCAT AGGATTAGAT TATAAAAAAA ATATAGCATA CACTAAAGAT    4200

GTATAGGTGC CATTTTTTAA TGTTGGCCAT ATTGTTTTTG AGCAATTTTT AATGCACCCT    4260

TTAGATTTCT TAGTCATCAA TTGAAATTAC ACATCCCCGG ATTTATCAAA AAAAAAAAA    4320

AAAAAAAAAA AAAAAA                                                    4337

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

His Xaa Xaa Glu His
1               5

(2) INFORMATION FOR SEQ ID NO:3:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Leu Lys Asn Gly Ile Arg Tyr Leu Ile Leu Pro Asn Lys Val Pro Pro
1               5                  10                  15

Thr Arg Phe Glu Ala His Met Glu Val His Val Gly Ser Ile Asp Glu
            20                  25                  30

Glu Asp Asp Glu Gln Gly Ile Ala His Met Ile Glu His Val Ala Phe
        35                  40                  45

Leu Gly Ser Lys Lys Arg Glu Lys Leu Leu Gly Thr Gly Ala Arg Ser
    50                  55                  60

Asn Ala Tyr Thr Asp Phe His Thr Val Phe His Ile His Ser Pro
65                  70                  75                  80

Thr Ser Thr Lys Asp Ser Asp Asp Leu Leu Pro Ser Val Leu Asp Ala
            85                  90                  95

Leu Asn Glu Ile Thr Phe His Pro Asn Phe Leu Ala Ser Arg Ile Glu
        100                 105                 110

Lys Glu Arg Arg Ala Ile Leu Ser Glu Leu Gln Met Met Asn Thr Ile
    115                 120                 125

Glu (2) INFORMATION FOR SEQ ID NO:4:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide
```

(vi) ORIGINAL SOURCE:
    (A) ORGANISM: Protease III (xi) SEQUENCE DESCRIPTION: SEQ ID NO:4:

```
Leu Asp Asn Gly Met Val Val Leu Val Ser Asp Pro Gln Ala Val
1               5                   10                  15

Lys Ser Leu Ser Ala Leu Val Val Pro Val Gly Ser Leu Glu Asp Pro
            20                  25                  30

Glu Ala Tyr Gln Gly Leu Ala His Tyr Leu Glu His Met Ser Leu Met
            35                  40                  45

Gly Ser Lys Lys Tyr Pro Gln Ala Asp Ser Leu Ala Glu Tyr Leu Lys
50                      55                  60

Met His Gly Gly Ser His Asn Ala Ser Thr Ala Pro Tyr Arg Thr Ala
65                      70                  75                  80

Phe Tyr Leu Glu Val Glu Asn Asp Ala Leu Pro Gly Ala Val Asp Arg
            85                  90                  95

Leu Ala Asp Ala Ile Ala Glu Pro Leu Leu Asp Lys Lys Tyr Ala Glu
            100                 105                 110

Arg Glu Arg Asn Ala Val Asn Ala Glu Leu Thr Met Ala Arg Thr Arg
            115                 120                 125

Asp
```

(2) INFORMATION FOR SEQ ID NO:5:

(i) SEQUENCE CHARACTERISTICS:
       (A) LENGTH: 129 amino acids
       (B) TYPE: amino acid
       (C) STRANDEDNESS: single
       (D) TOPOLOGY: linear (ii) MOLECULE TYPE: peptide (vi) ORIGINAL SOURCE:
       (A) ORGANISM: Human Insulin Degrading Enzyme (xi) SEQUENCE DESCRIPTION: SEQ ID NO:5:

```
Leu Ala Asn Gly Ile Lys Val Leu Leu Met Ser Asp Pro Thr Thr Asp
1               5                   10                  15

Lys Ser Ser Ala Ala Leu Asp Val His Ile Gly Ser Leu Ser Asp Pro
            20                  25                  30

Pro Asn Ile Ala Gly Leu Ser His Phe Cys Glu His Met Leu Phe Leu
            35                  40                  45

Gly Thr Lys Lys Tyr Pro Lys Glu Asn Glu Tyr Ser Gln Phe Leu Ser
50                      55                  60

Glu His Ala Gly Ser Ser Asn Ala Phe Thr Ser Gly Glu His Thr Asn
65                      70                  75                  80

Tyr Tyr Phe Asp Val Ser His Glu His Leu Glu Gly Ala Leu Asp Arg
            85                  90                  95

Phe Ala Gln Phe Phe Leu Cys Pro Leu Phe Asp Glu Ser Cys Lys Asp
            100                 105                 110

Arg Glu Val Asn Ala Val Asp Ser Glu His Glu Lys Asn Val Met Asn
            115                 120                 125

Asp
```

(2) INFORMATION FOR SEQ ID NO:6:

(i) SEQUENCE CHARACTERISTICS:
       (A) LENGTH: 136 amino acids

```
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: YDDC Swiss Protein P31828

(xi) SEQUENCE DESCRIPTION: SEQ ID NO:6:

Leu Asp Asn Gly Leu Arg Tyr Met Ile Tyr Pro His Ala His Pro Lys
1               5                   10                  15

Asp Gln Val Asn Leu Trp Leu Gln Ile His Thr Gly Ser Leu Gln Glu
            20                  25                  30

Glu Asp Asn Glu Leu Gly Val Ala His Phe Val Glu His Met Met Phe
        35                  40                  45

Asn Gly Thr Lys Thr Trp Pro Gly Asn Lys Val Ile Glu Thr Phe Glu
    50                  55                  60

Ser Met Gly Leu Arg Phe Gly Arg Asp Val Asn Ala Tyr Thr Ser Tyr
65                  70                  75                  80

Asp Glu Thr Val Tyr Gln Val Ser Leu Pro Thr Thr Gln Lys Gln Asn
            85                  90                  95

Leu Gln Gln Val Met Ala Ile Phe Ser Glu Trp Ser Asn Ala Ala Thr
            100                 105                 110

Phe Glu Lys Leu Glu Val Asp Ala Glu Arg Gly Val Ile Thr Glu Glu
            115                 120                 125

Trp Arg Ala His Gln Asp Ala Lys
            130                 135

(2) INFORMATION FOR SEQ ID NO:7:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: MPP B Subunit from Neurospora crassa (xi) SEQUENCE DESCRIPTION: SEQ ID NO:7:

Leu Lys Asn Gly Leu Thr Val Ala Ser Gln Tyr Ser Pro Tyr Ala Gln
1               5                   10                  15

Thr Ser Thr Val Gly Met Trp Ile Asp Ala Gly Ser Arg Ala Glu Thr
            20                  25                  30

Asp Glu Thr Asn Gly Thr Ala His Phe Leu Glu His Leu Ala Phe Lys
        35                  40                  45

Gly Thr Thr Lys Arg Thr Gln Gln Gln Leu Glu Leu Glu Ile Glu Asn
    50                  55                  60

Met Gly Ala His Leu Asn Ala Tyr Thr Ser Arg Glu Asn Thr Val Tyr
65                  70                  75                  80

Phe Ala Lys Ala Leu Asn Glu Asp Val Pro Lys Cys Val Asp Ile Leu
            85                  90                  95

Gln Asp Ile Leu Gln Asn Ser Lys Leu Glu Glu Ser Ala Ile Glu Arg
            100                 105                 110

Glu Arg Asp Val Ile Leu Arg Glu Ser Glu Glu Val Glu
            115                 120                 125
```

(2) INFORMATION FOR SEQ ID NO:8:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: MPP B Subunit from rat (xi) SEQUENCE DESCRIPTION: SEQ ID NO:8:

```
Leu Glu Asn Gly Leu Arg Val Ala Ser Glu Asn Ser Gly Ile Ser Thr
 1               5                  10                  15

Cys Thr Val Gly Leu Trp Ile Asp Ala Gly Ser Arg Tyr Glu Asn Glu
                20                  25                  30

Lys Asn Asn Gly Thr Ala His Phe Leu Glu His Met Ala Phe Lys Gly
            35                  40                  45

Thr Lys Lys Arg Ser Gln Leu Asp Leu Glu Leu Glu Ile Glu Asn Met
50                  55                  60

Gly Ala His Leu Asn Ala Tyr Thr Ser Arg Glu Gln Thr Val Tyr Tyr
65                  70                  75                  80

Ala Lys Ala Phe Ser Lys Asp Leu Pro Arg Ala Val Glu Ile Leu Ala
                85                  90                  95

Asp Ile Ile Gln Asn Ser Thr Leu Gly Glu Ala Glu Ile Glu Arg Glu
            100                 105                 110

Arg Gly Val Ile Leu Arg Glu Met Gln Glu Val Glu
        115                 120
```

(2) INFORMATION FOR SEQ ID NO:9:

(i) SEQUENCE CHARACTERISTICS:
        (A) LENGTH: 268 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ala Ser Thr Ser Thr Ser Ser Leu Ser Val Val Gly Thr Asn Leu Ser
 1               5                  10                  15

Leu Pro Pro His Arg His His Arg His Phe His Ser Pro Ser Ser Ile
                20                  25                  30

Ser Thr Arg Ile Arg Thr Asn Arg Leu Phe Leu Ser Ser Ser Leu Ala
            35                  40                  45

Phe Ser Ser Pro Arg Asp Ala Arg Val Val His Ala Gly Leu Gly Leu
50                  55                  60

Arg Arg Asn Thr Pro Asp Val Trp Lys His Tyr Ser Ser Val Leu Ser
65                  70                  75                  80

Gln Pro Thr Ala Pro Val Pro Val Arg Gln Ser Cys Thr Ser Cys Cys
                85                  90                  95

Leu Ala Ser Ala Lys Lys Arg Ser Asn Leu Pro Arg Phe Val Pro
            100                 105                 110

Gly Ala Phe Phe Asp Ser Ser Ser Phe Gly Leu Ser Lys Asp Lys Leu
        115                 120                 125

Arg His Ala Ser Val Lys Arg Val Gln Leu Pro His Ala Thr Val Gly
        130                 135                 140
```

```
Pro Asp Glu Pro His Ala Ala Ser Thr Thr Trp Gln Glu Gly Val Ala
145                 150                 155                 160

Glu Lys Gln Asp Leu Ser Leu Phe Asp Ser Glu Leu Glu Arg Leu Glu
            165                 170                 175

Gly Phe Leu Gly Ser Glu Leu Pro Ser His Pro Lys Leu His Arg Gly
            180                 185                 190

Gln Leu Lys Asn Gly Ile Arg Tyr Leu Ile Leu Pro Asn Lys Val Pro
            195                 200                 205

Pro Thr Arg Phe Glu Ala His Met Glu Val His Val Gly Ser Ile Asp
210                 215                 220

Glu Glu Asp Asp Glu Gln Gly Ile Ala His Met Ile Glu His Val Ala
225                 230                 235                 240

Phe Leu Gly Ser Lys Lys Arg Glu Lys Leu Leu Gly Thr Gly Ala Arg
            245                 250                 255

Ser Asn Ala Tyr Thr Asp Phe His His Thr Val Phe
            260                 265

(2) INFORMATION FOR SEQ ID NO:10:

(i) SEQUENCE CHARACTERISTICS:
        (A) LENGTH: 297 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ala Ser Ser Ser Ser Ile Phe Thr Gly Val Lys Phe Ser Pro Ile
1               5                   10                  15

Leu Ala Pro Phe Asn Ser Gly Asp Ser Arg Arg Ser Arg Tyr Leu Lys
            20                  25                  30

Asp Ser Arg Asn Lys Val Arg Phe Asn Pro Ser Ser Pro Arg Leu Thr
            35                  40                  45

Pro His Arg Val Arg Val Glu Ala Pro Ser Leu Ile Pro Tyr Asn Gly
            50                  55                  60

Leu Trp Tyr Val Ser Val Phe Ser Phe Val Phe Met Glu Thr Glu Leu
65                  70                  75                  80

Val Leu Gly Ser Lys Phe Cys Val Gln Leu Asn Arg Phe Val Lys Phe
            85                  90                  95

Cys Val Glu Phe Cys Gly Val Lys Gly Ala Gln Pro Asn Ser His Lys
            100                 105                 110

Gly Arg Leu Lys Arg Asn Ile Val Ser Gly Lys Glu Ala Thr Gly Tyr
            115                 120                 125

His Phe Leu Lys Asp Val Ile Ser Val Leu Val Lys Gly Ile Lys
            130                 135                 140

Leu Glu Ser Glu Glu His Tyr Leu Val Pro Leu Trp Ile Glu Leu His
145                 150                 155                 160

Leu Val Cys Arg Gly Arg Ala Thr Leu Gly Pro Asp Glu Pro His Ala
            165                 170                 175

Ala Gly Thr Ala Trp Pro Asp Gly Ile Val Ala Glu Arg Gln Asp Leu
            180                 185                 190

Asp Leu Leu Pro Pro Glu Ile Asp Ser Ala Glu Leu Glu Ala Phe Leu
            195                 200                 205

Gly Cys Glu Leu Pro Ser His Pro Lys Leu His Arg Gly Gln Leu Lys
            210                 215                 220
```

```
Asn Gly Leu Arg Tyr Leu Ile Leu Pro Asn Lys Val Pro Pro Ala Arg
225                 230                 235                 240

Phe Glu Ala His Met Glu Val His Val Gly Ser Ile Asp Glu Glu Glu
            245                 250                 255

Asp Glu Gln Gly Ile Ala His Met Ile Glu His Val Ala Phe Leu Gly
            260                 265                 270

Ser Lys Lys Arg Glu Lys Leu Leu Gly Thr Gly Ala Arg Ser Asn Ala
            275                 280                 285

Tyr Thr Asp Phe His His Thr Val Phe
    290                 295
```

(2) INFORMATION FOR SEQ ID NO:11:

(i) SEQUENCE CHARACTERISTICS:
        (A) LENGTH: 2341 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis CPE (xi) SEQUENCE DESCRIPTION: SEQ ID NO:11:

```
GAAAACTCAT GATCGCCAAG TTGAAATAGT ATAGAAAGCC TAGTTTAGAG TGACAAACAA    60
CACTTGAAAT CCTAAACAAT CGATCTTGTA ACCACTATTG CACATCACCA CAAAACACAC   120
ATTATCTGAC GAAAGCTAAT CACATTCAAA TGATTAAACC AAAATAACAG AATCTAAACA   180
TTAATTAACT TATATTCGAG ATACAACGAG ACCTATACGA GTTTGAATGA AAGACAATTT   240
TCTTGTCTAC TATATGTACA AGAAAAAATA GAGATCATAC AAATAGCTTT TCTTCTAACT   300
ATCGAAATCA ATATTCTTAT AATTAGGCAT GAATCCTTTA AAAATTTAGG GGTCATGTAA   360
CACTTAACAT AAGCAAATAT ATGAATGCAT AAAATTATTA ACTTTTCGAT CATTTTTTTA   420
AAAAATTATA ATTTTCGGCA AACGGTATTT AAACCAAATT TCACAAAATT ACATCAATTT   480
TTTTTTTAGA TTGCTATCTA AGCCCTTAAC CGAAATACCT AAACCTAATT GAACCGATCA   540
GTTCAAAGTT GCCAGCAGAT AAACAATGTT TCATGTCCG ACTCTATACTC CATAGTCGAA   600
CGTTAACCCT GAAGAAACAT ATTTCCAGTG AAGGTTTAGT CTTAAATCTA CCAATATAAC   660
CAGAAAAATC CAGAAAAAAC TTGCCATTAA CTACCGCATG ATCAACCGGT TAAAACTTCT   720
GGGTGAAAAT CTTTCCAAAA TATTGAGATT TTGACTTCAA ACCCTTTGCT ACAAATAGAA   780
GGTTTGATTT TGGAATTAAA ATATATAGTT TGTATTAAAA AAGAAAGAAA CATTAATATA   840
CTCATATAAA AAGAGTTTAA CAAAATAAAA ATCAGGAAGG AGAAGACAAT AAAACGTAGC   900
TAACCTCATC TCCCTCTTCT TTTTTTTTG TTCTTTAATA GTTTCCGTCT CTCTTTTTTC   960
TCCTCCACCT CTCCTTTGTC CTCAATAGCC GACGATGGCT TCATCGTCCT CTTCCATTTT  1020
CACCGGTGTT AAGTTCTCTC CGATCTTAGC TCCCTTTAAC TCCGGAGATA GCCGCCGCTC  1080
TCGATATCTA AAAGATAGCC GGAATAAAGT TAGGTTTAAT CCATCGTCGC CGCGTCTCAC  1140
TCCTCATCGT GTTCGCGTCG AAGCTCCGTC TTTAATTCCC TATAATGGTC TTTGGTACGT  1200
ATCAGTTTTC AGCTTCGTGT TCATGGAAAC TGAATTAGTT CTTGGTTCAA AATTTTGTTG  1260
AGTTCAGTTA AATCGATTTG TTAAATTTTG TGTTGAATTT TGTGGTGTTA AGGGCGCGCA  1320
```

-continued

```
GCCAAATTCG CATAAGGGAC GTTTAAAGAG GAACATTGTT TCGGGAAAAG AAGCTACCGG    1380

ATATCACTTT CTCAAGGACG TAATTTCTGT CTTACTTGTA AAAGGAATCA AGCTGGAATC    1440

AGAAGAGCAT TACCTAGTGC CTTTGTGGAT AGAACTGCAT TTAGTTTGTC GAGGTCGAGT    1500

TTGACATCTT CTCTGGTAAG TAAGCTACAT CATTTACTTT CTATGTTCTT GTCTTGTGCT    1560

TGTTTGATTT ATCTCTGTTA ACTGACTCAA CATGTGCAGA GAAACATTCT CAGATTGTGA    1620

TGCAACTCTT GGACCAGATG AGCCACATGC TGCTGGTACA GCTTGGCCTG ATGGTATTGT    1680

TGCGGAGAGA CAAGATCTCG ACTTATTGCC TCCTGAGATT GATAGTGCAG AGCTAGAAGC    1740

GTTTCTTGGT TGTGAACTTC CTTCTCATCC AAAGTTGCAC CGGGGTCAAT TGAAAAATGT    1800

GCTTCGATAT CTTATTTTGC CAAACAAAGT TCCACCGAAC AGGTAAATTG AGTAGAATGC    1860

TCGAAGTTGG TCTACTTGTG ATACTCTTAA TGACAATATA TCATTCCTTG AAAACCGGTA    1920

AGCAAAATGG TTATAGCTTA ACCATATGGT GGAATCCTTA AGGTCTTCCT GCTATATCTT    1980

ATTTGAGTTT GGAAATGTTT TCAATGCTAG ATTTGAGGCA CACATGGAAG TTCATGTAGG    2040

ATCGATTGAT GAGGAAGAAG ATGAGCAAGG GATTGCTCAT ATGATAGAAC ATGTTGCTTT    2100

CCTTGGGAGC AAGAAACGTG AGAAACTTCT TGGTACAGGT GCCCGCTCTA ATGCCTACAC    2160

CGATTTCCAC CATACAGTAT TTATATTCAT TCTCCAACCC ACACGAAGGT TTGTTCTCTT    2220

CTACACCTAT TGGCGTATTT AGTGATGTAT CTTTTTCTTG GTTAGTTCAA TTCACAGGTT    2280

TTTATTGCCT CGTATTTACT TTAACAAATA TGGTGTTTAT AGTCTATATC TATATGTTGC    2340

A                                                                    2341
```

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
His Met Ile Glu His
1               5
```

(2) INFORMATION FOR SEQ ID NO:13:

(i) SEQUENCE CHARACTERISTICS:
        (A) LENGTH: 1259 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Met Pro Met Ala Ala Ser Thr Ser Thr Ser Ser Leu Ser Val Val Gly
1               5                   10                  15

Thr Asn Leu Ser Leu Pro Pro His Arg His Arg His Phe His Ser
            20                  25                  30

Pro Ser Ser Ile Ser Thr Arg Ile Arg Thr Asn Arg Leu Phe Leu Ser
            35                  40                  45

Ser Ser Leu Ala Phe Ser Ser Pro Arg Asp Ala Arg Val Val His Ala
            50                  55                  60

Gly Leu Gly Leu Arg Arg Asn Thr Pro Asp Val Trp Lys His Tyr Ser
65                  70                  75                  80
```

```
Ser Val Leu Ser Gln Pro Thr Ala Pro Val Pro Val Arg Gln Ser Cys
                85                  90                  95
Thr Ser Cys Cys Leu Ala Ser Ala Lys Lys Arg Arg Ser Asn Leu Pro
            100                 105                 110
Arg Phe Val Pro Gly Ala Phe Phe Asp Ser Ser Phe Gly Leu Ser
        115                 120                 125
Lys Asp Lys Leu Arg His Ala Ser Val Lys Arg Val Gln Leu Pro His
    130                 135                 140
Ala Thr Val Gly Pro Asp Glu Pro His Ala Ala Ser Thr Thr Trp Gln
145                 150                 155                 160
Glu Gly Val Ala Glu Lys Gln Asp Leu Ser Leu Phe Asp Ser Glu Leu
                165                 170                 175
Glu Arg Leu Glu Gly Phe Leu Gly Ser Glu Leu Pro Ser His Pro Lys
            180                 185                 190
Leu His Arg Gly Gln Leu Lys Asn Gly Ile Arg Tyr Leu Ile Leu Pro
        195                 200                 205
Asn Lys Val Pro Pro Thr Arg Phe Glu Ala His Met Glu Val His Val
    210                 215                 220
Gly Ser Ile Asp Glu Glu Asp Glu Gln Gly Ile Ala His Met Ile
225                 230                 235                 240
Glu His Val Ala Phe Leu Gly Ser Lys Lys Arg Glu Lys Leu Leu Gly
                245                 250                 255
Thr Gly Ala Arg Ser Asn Ala Tyr Thr Asp Phe His His Thr Val Phe
            260                 265                 270
His Ile His Ser Pro Thr Ser Thr Lys Asp Ser Asp Leu Leu Pro
        275                 280                 285
Ser Val Leu Asp Ala Leu Asn Glu Ile Thr Phe His Pro Asn Phe Leu
    290                 295                 300
Ala Ser Arg Ile Glu Lys Glu Arg Ala Ile Leu Ser Glu Leu Gln
305                 310                 315                 320
Met Met Asn Thr Ile Glu Tyr Arg Val Asp Cys Gln Leu Leu Gln His
                325                 330                 335
Leu His Ser Glu Asn Lys Leu Ser Lys Arg Phe Pro Ile Gly Leu Glu
            340                 345                 350
Glu Gln Ile Lys Lys Trp Asp Ala Asp Lys Ile Arg Lys Phe His Glu
        355                 360                 365
Arg Trp Tyr Phe Pro Ala Asn Ala Thr Leu Tyr Ile Val Gly Asp Ile
    370                 375                 380
Gly Asn Ile Pro Lys Thr Val Asn Gln Ile Glu Ala Val Phe Gly Gln
385                 390                 395                 400
Thr Gly Val Asp Asn Glu Lys Gly Ser Val Ala Thr Ser Ser Ala Phe
                405                 410                 415
Gly Ala Met Ala Ser Phe Leu Val Pro Lys Leu Ser Val Gly Leu Gly
            420                 425                 430
Gly Asn Ser Ile Glu Arg Pro Thr Asn Thr Thr Asp Gln Ser Lys Val
        435                 440                 445
Phe Lys Lys Glu Arg His Ala Val Arg Pro Val Lys His Thr Trp
    450                 455                 460
Ser Leu Pro Gly Ser Ser Ala Asn Leu Lys Pro Pro Gln Ile Phe Gln
465                 470                 475                 480
His Glu Leu Leu Gln Asn Phe Ser Ile Asn Met Phe Cys Lys Ile Pro
                485                 490                 495
```

-continued

```
Val Asn Lys Val Gln Thr Tyr Arg Asp Leu Arg Ile Val Leu Met Lys
            500                 505                 510

Arg Ile Phe Leu Ser Ala Leu His Phe Arg Ile Asn Thr Arg Tyr Lys
        515                 520                 525

Ser Ser Asn Pro Pro Phe Thr Ser Val Glu Leu Asp His Ser Asp Ser
    530                 535                 540

Gly Arg Glu Gly Cys Thr Val Thr Thr Leu Thr Ile Thr Ala Glu Pro
545                 550                 555                 560

Lys Asn Trp Gln Asn Ala Ile Arg Val Ala Val His Glu Val Arg Arg
                565                 570                 575

Leu Lys Glu Phe Gly Val Thr Gln Gly Glu Leu Thr Arg Tyr Leu Asp
            580                 585                 590

Ala Leu Leu Arg Asp Ser Glu His Leu Ala Ala Met Ile Asp Asn Val
        595                 600                 605

Ser Ser Val Asp Asn Leu Asp Phe Ile Met Glu Ser Asp Ala Leu Gly
    610                 615                 620

His Lys Val Met Asp Gln Ser Gln Gly His Glu Ser Leu Ile Ala Val
625                 630                 635                 640

Ala Gly Thr Val Thr Leu Asp Glu Val Asn Ser Val Gly Ala Gln Val
                645                 650                 655

Leu Glu Phe Ile Ala Asp Phe Gly Lys Leu Ser Ala Pro Leu Pro Ala
            660                 665                 670

Ala Ile Val Ala Cys Val Pro Lys Lys Val His Ile Glu Gly Ala Gly
        675                 680                 685

Glu Thr Glu Phe Lys Ile Ser Ser Thr Glu Ile Thr Asp Ala Met Lys
    690                 695                 700

Ala Gly Leu Asp Glu Pro Ile Glu Pro Glu Pro Glu Leu Glu Val Pro
705                 710                 715                 720

Lys Glu Leu Val Gln Ser Ser Thr Leu Gln Glu Leu Lys Asn Gln Arg
                725                 730                 735

Lys Pro Ala Phe Ile Pro Val Ser Pro Glu Ile Glu Ala Lys Lys Leu
            740                 745                 750

His Asp Glu Glu Thr Gly Ile Thr Arg Leu Arg Leu Ala Asn Gly Ile
        755                 760                 765

Pro Val Asn Tyr Lys Ile Ser Lys Ser Glu Thr Gln Ser Gly Val Met
    770                 775                 780

Arg Leu Ile Val Gly Gly Gly Arg Ala Ala Glu Gly Ser Asp Ser Arg
785                 790                 795                 800

Gly Ser Val Ile Val Gly Val Arg Thr Leu Ser Glu Gly Gly Arg Val
                805                 810                 815

Gly Asn Phe Ser Arg Glu Gln Val Glu Leu Phe Cys Val Asn Asn Gln
            820                 825                 830

Ile Asn Cys Ser Leu Glu Ser Thr Glu Glu Phe Ile Ser Leu Glu Phe
        835                 840                 845

Arg Phe Thr Leu Arg Asn Asn Gly Met Arg Ala Ala Phe Gln Leu Leu
    850                 855                 860

His Met Val Leu Glu His Ser Val Trp Ser Asp Asp Ala Leu Asp Arg
865                 870                 875                 880

Ala Arg Gln Val Tyr Leu Ser Tyr Tyr Arg Ser Ile Pro Lys Ser Leu
                885                 890                 895

Glu Arg Ser Thr Ala His Lys Leu Met Val Ala Met Leu Asp Gly Asp
            900                 905                 910

Glu Arg Phe Thr Glu Pro Thr Pro Ser Ser Leu Glu Asn Leu Thr Leu
```

|  | 915 |  |  | 920 |  |  | 925 |  |  |  |  |
|---|---|---|---|---|---|---|---|---|---|---|---|

Gln Ser Val Lys Asp Ala Val Met Asn Gln Phe Val Gly Asn Asn Met
    930               935              940

Glu Val Ser Ile Val Gly Asp Phe Thr Glu Glu Ile Glu Ser Cys
945               950              955              960

Ile Leu Asp Tyr Leu Gly Thr Ala Gln Ala Thr Gly Asn Phe Lys Asn
             965              970              975

Gln Gln Gln Ile Ile Pro Pro Thr Phe Arg Leu Ser Pro Ser Ser Leu
             980              985              990

Gln Ser Gln Glu Val Phe Leu Asn Asp Thr Asp Glu Arg Ala Cys Ala
        995              1000            1005

Tyr Ile Ala Gly Pro Ala Pro Asn Arg Trp Gly Phe Thr Ala Asp Gly
    1010            1015             1020

Asn Asp Leu Leu Glu Thr Ile Asp Asn Ala Ser Ser Val Asn Asn Asn
1025            1030            1035            1040

Gly Thr Lys Ser Asp Ala Leu Gln Thr Glu Gly Ala Pro Arg Arg Ser
            1045            1050            1055

Leu Arg Ser His Pro Leu Phe Phe Gly Ile Thr Met Gly Leu Leu Ser
            1060            1065            1070

Glu Ile Ile Asn Ser Arg Leu Phe Thr Thr Val Arg Asp Ser Leu Gly
        1075            1080            1085

Leu Thr Tyr Asp Val Ser Phe Glu Leu Asn Leu Phe Asp Arg Leu Lys
    1090            1095            1100

Leu Gly Trp Tyr Val Val Ser Val Thr Ser Thr Pro Ser Lys Val His
1105            1110            1115            1120

Lys Ala Val Asp Ala Cys Lys Asn Val Leu Arg Gly Leu His Ser Asn
            1125            1130            1135

Gly Ile Thr Val Arg Glu Leu Asp Arg Ala Lys Arg Thr Leu Leu Met
        1140            1145            1150

Arg His Glu Ala Glu Ile Lys Ser Asn Ala Tyr Trp Leu Gly Leu Leu
        1155            1160            1165

Ala His Leu Gln Ser Ser Ser Val Pro Arg Lys Asp Leu Ser Cys Ile
    1170            1175            1180

Lys Asp Leu Thr Ser Leu Tyr Glu Ala Ala Thr Ile Glu Asp Thr Cys
1185            1190            1195            1200

Leu Ala Tyr Glu Gln Leu Lys Val Asp Glu Asp Ser Leu Tyr Ser Cys
            1205            1210            1215

Ile Gly Val Ser Gly Ala Gln Ala Ala Gln Asp Ile Ala Ala Pro Val
            1220            1225            1230

Glu Glu Glu Glu Ala Gly Glu Gly Tyr Pro Gly Val Leu Pro Met Gly
        1235            1240            1245

Arg Gly Leu Ser Thr Met Thr Arg Pro Thr Thr
    1250            1255